US011346705B2

United States Patent
Khokhar

(10) Patent No.: US 11,346,705 B2
(45) Date of Patent: May 31, 2022

(54) METHODS AND SYSTEMS FOR INTERACTIVE WEIGHT MANAGEMENT

(71) Applicant: Rasimo Systems LLC, Raleigh, NC (US)

(72) Inventor: Sarfraz Khokhar, Raleigh, NC (US)

(73) Assignee: Rasimo Systems LLC, Raleigh, NC (US)

( * ) Notice: Subject to any disclaimer, the term of this patent is extended or adjusted under 35 U.S.C. 154(b) by 463 days.

(21) Appl. No.: 16/258,511

(22) Filed: Jan. 25, 2019

(65) Prior Publication Data

US 2019/0226907 A1 Jul. 25, 2019

Related U.S. Application Data

(60) Provisional application No. 62/621,860, filed on Jan. 25, 2018.

(51) Int. Cl.
*G01G 19/414* (2006.01)
*G16H 20/60* (2018.01)
(Continued)

(52) U.S. Cl.
CPC ......... *G01G 19/4146* (2013.01); *G01G 19/44* (2013.01); *G16H 20/60* (2018.01); *G16H 10/20* (2018.01); *G16H 10/60* (2018.01)

(58) Field of Classification Search
None
See application file for complete search history.

(56) References Cited

U.S. PATENT DOCUMENTS

| 2006/0015016 A1* | 1/2006 | Thornton ........... G01G 19/4146 600/300 |
| 2007/0168230 A1 | 7/2007 | Roman |

(Continued)

FOREIGN PATENT DOCUMENTS

WO 2008011667 A1 1/2008

OTHER PUBLICATIONS

Thomas, Diana M.; Martin, Corby K.; Heymsfield, Steven; Redman, Leanne M.; Schoeller, Dale A.; Levine, James A.; "A Simple Model Predicting Individual Weight Change in Humans;" Apr. 4, 2014; p. 1-25 (Year: 2014).*

(Continued)

*Primary Examiner* — Arleen M Vazquez
*Assistant Examiner* — Terence E Stifter, Jr.
(74) *Attorney, Agent, or Firm* — Dicke, Billig & Czaja, PLLC

(57) ABSTRACT

A computer implemented method for interactive weight management that includes generating a number of sub-goal weights $g_0, g_1, \ldots g_n$ based on a current weight $C_w$, a desired weight loss amount ($\Delta W$), a desired weight $D_w$, a curve tension r, and a timeframe ($\tau$) in which the weight loss amount ($\Delta W$) is to be achieved, wherein the timeframe ($\tau$) includes a number (n) of time periods that each correspond with a pair of successive ones of the sub-goal weights $g_0, g_1, \ldots g_n$. The method includes sending the sub-goal weights $g_0, g_1, \ldots g_n$ and the number (n) of time periods to a weight measuring device that is associated with a user. Based on the condition $W_{a1} > g_i < W_{a2}$ or based on the condition $$W_{a1} < \frac{g_i + g_{i+1}}{2} \text{ and } W_{a2} < \frac{g_{i+1} + g_{i+2}}{2},$$

(Continued)

new sub-goal weights $g_0, g_1, \ldots g_n$ are generated and are updated in the weighing device.

20 Claims, 11 Drawing Sheets

(51) Int. Cl.
  *G01G 19/44* (2006.01)
  *G16H 10/60* (2018.01)
  *G16H 10/20* (2018.01)

(56) References Cited

U.S. PATENT DOCUMENTS

| | | | |
|---|---|---|---|
| 2008/0306767 A1 | 12/2008 | Bodlaender et al. | |
| 2013/0198214 A1* | 8/2013 | Hall | G16H 20/60 707/758 |
| 2014/0344192 A1* | 11/2014 | Akai | G16H 20/60 706/11 |
| 2015/0107910 A1* | 4/2015 | Villard | G16H 20/60 177/25.12 |
| 2016/0109282 A1 | 4/2016 | Sharma | |
| 2016/0171905 A1 | 6/2016 | Nusbaum et al. | |
| 2016/0324468 A1* | 11/2016 | Kwon | G01G 23/3742 |
| 2017/0330155 A1 | 11/2017 | Rana | |
| 2018/0294053 A1* | 10/2018 | Runyon | G06F 3/04817 |

OTHER PUBLICATIONS

International Search Report and Written Opinion of the International Searching Authority for Application No. PCT/US2019/15306 dated Apr. 16, 2019 (7 pages).

* cited by examiner

METHODS AND SYSTEMS FOR INTERACTIVE WEIGHT MANAGEMENT

CROSS-REFERENCE TO RELATED APPLICATION

This application is a non-provisional of U.S. application Ser. No. 62/621,860, filed Jan. 25, 2018, which is herein incorporated by reference.

FIELD OF TECHNOLOGY

The embodiments described herein relate to a system that collects minimum data about an individual and utilizes the data to provide a guided system that assists individuals to audit and manage their weight loss. The systems described herein provide individuals with a series of sub-goals, and in pursuit of these sub-goals, the individuals reach their desired weight loss goal, and if an individual loses track, the system brings the individual back on track. Once an individual reaches the target goal, the system registers the individual into a maintenance program. When the individual gains weight during maintenance mode, the individual is put back into weight loss mode. The systems described herein also provide individuals with accountability and quick feedback.

BACKGROUND

Weight management is of high importance and focus area among most of the people. People have been told for decades to eat healthy and stay active, and people tend to do most of it, however they get lost in their weight management effort mainly because they make large goals and they don't have a system to assist them in reaching their healthy weight and stay there, and there is not firm accountability framework in their self-design effort. Once they lose track it becomes hard for them to come back—this is where an overweight individual starts becoming obese and obese start becoming extremely obese.

According to national Institute of Diabetes and Digestive and Kidney Diseases, excess weight may increase the risk for many health problems, including
- type 2 diabetes
- high blood pressure
- heart disease and strokes
- certain types of cancer
- sleep apnea
- osteoarthritis
- fatty liver disease
- kidney disease
- pregnancy problems, such as high blood sugar during pregnancy, high blood pressure, and increased risk for cesarean delivery (C-section)

In the US 70.2% (2013-2014 study) of the adult population is overweight or obese (men being 73.7% and women being 66.9%). US weight loss market (as of Dec. 20, 2017) worth $66 billion. Currently, estimates for healthcare costs stemming from obesity range from $147 billion to nearly $210 billion per year. In addition, obesity is associated with job absenteeism, costing approximately $4.3 billion annually and with lower productivity while at work, costing employers $506 per obese worker per year.

Self-monitoring is the centerpiece of behavioral weight loss intervention programs. There are three major discipline one has to deal with: diet, exercise and self-weighing management. A significant association between self-monitoring and weight loss has been consistently established in various studies. The following facts would help in a weight loss effort:
- Self-weighing in pursuit of specific interim (short-term) goals and a long-term goal is very effective.
- Quick feedback and coaching on individual's results at regular intervals during the process is the key differentiator—it facilitates individual's accountability and responsibility.
- Food intake and physical activity are the most focused attributes for weight management. No doubt, they are the key factors. Yet millions of people have been doing these routines for years and they don't get desired results. What they are missing is handling the weight management process effectively. Accountability is one of the key factors. Without a proper framework, following the process scientifically is not easy and is time consuming.

What is desired is a system that provides individuals short term goals which should become the focus for the time being.

What is desired is a system that readjusts the interim goals should an individual couldn't achieve the set interim goals. Such readjustments are adaptive to the individual performance.

What is desired is a system that incorporate quick feedback to the individual, it could be informative, persuasive, corrective or reinforcement feedback.

What is desired is a system that provides a framework for accountability for the individuals before friends and family regardless how far apart they live.

What is desired a weighing device that could show the individuals their sub-goals, progress on the sub-goals, and the overall progress on the weight management effort along with current weight.

For these and other reasons, there is a need for the present invention.

SUMMARY

According to an embodiment of a method, the method includes generating a number of sub-goal weights $g_0, g_1, \ldots g_n$ based on a current weight $C_w$, a desired weight loss amount ($\Delta W$), a desired weight $D_w$, a curve tension r which is set to an initial value that is greater than zero, and a timeframe ($\tau$) in which the weight loss amount ($\Delta W$) is to be achieved, wherein the timeframe ($\tau$) includes a number (n) of time periods that each correspond with a pair of successive ones of the sub-goal weights $g_0, g_1, \ldots g_n$ such that sub-goal weight $g_0$ corresponds with a beginning of the first one of the number (n) of time periods and sub-goal weight $g_n$ corresponds with an end of the last one of the number (n) of time periods. The method includes generating sub-goal weights $g_0, g_1, \ldots g_n$ by using the sub-goal generation formulas:

$$g_0 = W_0 + D_w = \frac{\Delta W}{1 - e^{-\frac{n}{10}}}\left(e^{\frac{0}{10}} - e^{-\frac{n}{10}}\right) + D_w = C_w,$$

$$g_1 = W_1 + D_w = \frac{\Delta W}{1 - e^{-\frac{n}{10}}}\left(e^{\frac{-r}{10}} - e^{-\frac{n}{10}}\right) + D_w,$$

$$g_2 = W_2 + D_w = \frac{\Delta W}{1 - e^{-\frac{n}{10}}}\left(e^{\frac{-2r}{10}} - e^{-\frac{n}{10}}\right) + D_w, \text{ and}$$

-continued $$g_n = W_n + D_w = \frac{\Delta W}{1 - e^{-\frac{n}{10}}}\left(e^{\frac{-nr}{10}} - e^{-\frac{n}{10}}\right) + D_w = D_w;$$

The method includes sending the sub-goal weights $g_0, g_1, \ldots g_n$ and the number of time periods that each correspond with the pair of successive ones of the sub-goal weights $g_0, g_1, \ldots g_n$ to a weight measuring device that is associated with a user. The method includes receiving one of a number of measured weights $W_0, W_1, \ldots W_n$ from the weight measuring device that is associated with the user, where each one of the number of measured weights $W_0, W_1, \ldots W_n$ is associated with a corresponding one of the number of sub-goal weights $g_0, g_1, \ldots g_n$ for a same one of the number (n) of time periods, and where each one of the sub-goal weights $g_0, g_1, \ldots g_n$ represents a short term desired weight for an associated one of the number of measured weights $W_0, W_1, \ldots W_n$.

Based on the condition $W_{a1} > g_i < W_{a2}$ or based on the condition $$W_{a1} < \frac{g_i + g_{i+1}}{2} \text{ and } W_{a2} < \frac{g_{i+1} + g_{i+2}}{2},$$

new sub-goal weights $g_0, g_1, \ldots g_n$ are generated and are updated in the weighing device.

Those skilled in the art will recognize additional features and advantages upon reading the following detailed description, and upon viewing the accompanying drawings.

BRIEF DESCRIPTION OF THE DRAWINGS

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows.

FIG. 1 also shows how user gets feedback on mobile devices and desktop.

FIG. 1 also demonstrate how the users reach accountability circle and its features.

FIG. 3 depicts more weight loss in early sub-goals as compared to the trailing sub-goals.

DETAILED DESCRIPTION

Figure 1:
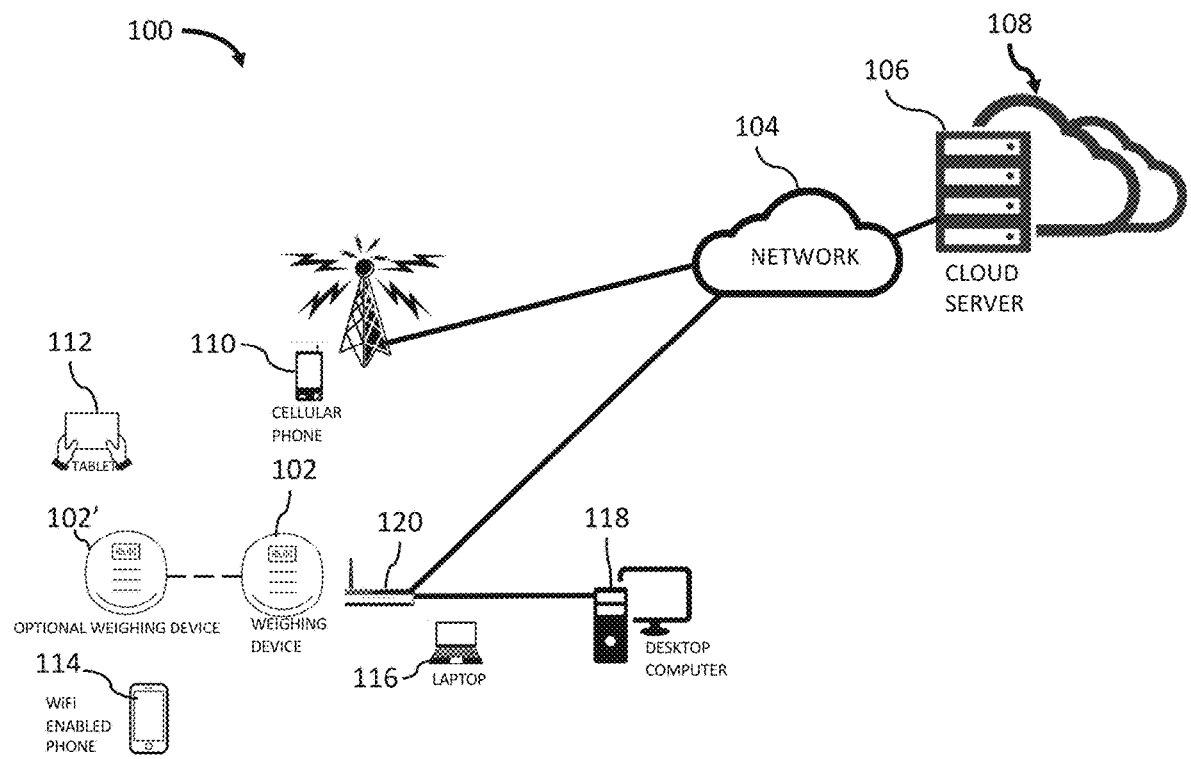
FIG. 1 shows the overall system architecture in which weighing device is integrated and communicates with the cloud server, sends the current weight and receives sub-goals and overall performance and displays on its screen.

In the embodiments illustrated herein, a system is described for effective weight management which provides a framework for cognizant individuals and individuals who have little exposure to weight management knowledge. The system includes a weight measuring intelligent wirelessly connected device, a cloud server to which the device can communicate, and a hand-held mobile device. In various embodiments, algorithms and data reside on one or more cloud servers or cloud-based platforms. In operation, the server pushes an individual's weight loss interim sub-goals to a weight measuring device where the goals are displayed on a Graphical User Interface (GUI) on the device for the individual. In one embodiment, the user device is a mobile device which can receive immediate feedback from the server in regard to the current status of the individual's weight loss progress and also can also access an individual's dashboard residing on the server. In one embodiment, the dashboard is displayed on a GUI of a device such as a mobile device. An individual can view the dashboard and communicate with the server through a common computing device with a screen. In one embodiment, the dashboard is displayed on a GUI of a wireless or cellular connected device such as a cellular phone 110, a tablet 112, a WiFi enabled phone, a wireless or cellular connected weighing device 102, a laptop computer 116 or a desktop computer 118.

In the illustrated embodiments, the weight management system described herein provides an intelligent framework in which individuals are provided with weight loss sub-goals to be achieved, where the current weight loss sub-goals are displayed on the weighing device and/or other user devices as described above. If the individual cannot keep with the current series of sub-goals, or if the sub-goals are too easy to achieve, the weight management system detects this behavior and assigns the individual another set of sub-goals until the individual reaches his/her desired target weight goal. After the individual reaches his/her target weight, the weight management system places the individual on a long-term weight maintenance plan.

In the illustrated embodiments, the intelligent weighing device is an integral part of the weight management system. The device displays to the individual his/her current sub-goal, the individual's standing in reaching the sub-goal, and the overall achievement in reaching the target weight, along with current weight and Body Mass Index (BMI).

In yet another aspect, the system provides a framework in which the individual can choose a desired target weight and the time period in which the desired weight is to be achieved.

In yet another aspect, if the individual sets unrealistic goals in terms of target weight and the time to reach the target weight, the system suggests a realistic target weight loss goal and corresponding interim weight loss sub-goals for the time in which the desired target weight is to be achieved. It is left to individual's discretion if he/she accepts the new target weight loss goal and corresponding interim weight loss sub-goals recommended by the weight management system or keeps his/her previous weight loss goal and the time in which he/she desires to reach the target weight.

In yet another aspect, the system provides a quick feedback to the individual, corrective or reinforcing based on the individual's progress.

In yet another aspect, if the individual insists on his/her prescribed target weight and time, the system accepts it and provide to the individual most suitable sub-goals.

In yet another aspect, if the individual has not weighed himself/herself within a unit of time selected by the individual (e.g., one week), the system sends reminders to the individual to persuade him/her to step on the device for weighing.

In yet another aspect of the weight management system, the system provides accountability framework to the individual before the system itself, friends and family. In various embodiments, Friends and family can be located remotely.

When Individuals realize and attempt to lose their weight, they commonly focus on diet and physical activity, which of course are the key for losing weight. These facts are known to human for decades, yet the overall weight epidemic is ever increasing. It does not mean people don't attempt to lose weight, they do, and the weight loss market of $66 billion clearly demonstrates this. What is missing an effective framework which guides and assists people in reaching their desired target weight. People tend to start a weight loss program with a high level of enthusiasm, but get lost in their pursuit of achieving their target weight. The first issue is people tend to set a large goal to reach, which may take quite a long a time, where the probability of getting lost during the pursuit of the target weight is high. Secondly, when people become a bit uninterested, or fed up, they tend not to weigh themselves often enough and their weight drifts upwards to higher numbers.

In another embodiment, the weight management system provides an accountability framework, referred to herein as an accountability circle. Individuals can get lost on their path to achieving their desired target weight when they are not accountable to any entity. Self-accountability is no accountability. An effective accountability framework is provided by the weight management system that allows individuals to choose their accountability circle members.

In another embodiment, the weight management system provides individuals with their most suitable sub-goals, an accountability mechanism, and timely feedback and coaching to enable the individuals to remedy any current issues that they may have with their weight loss effort. In the absence of this feedback and instant coaching, an individual or user is more likely to lose focus and lose interest.

FIG. 1 illustrates a system architecture at 100 in which weighing device 102 is integrated and communicates with the cloud server 106 via a network 104. Weighing device 102 is a weight scale and is configured to send the current weight of a user to weight management service 108 hosted on cloud server 106 and receive sub-goals and overall performance information. In some embodiments, weighing device 102 is able to display the sub-goal and performance information on a screen display that is located on weighing device 102. FIG. 1 illustrates additional embodiments of how users are able to receive feedback information from weight management service 108, on mobile devices and desktop computers. The feedback information may include sub-goals, overall performance, and body composition by percentage or weight of muscle, fats, bones, and water hydration information, along with constructive feedback and further instructions needed to reach their target weight. FIG. 1 illustrates a cellular phone 110, a tablet 112, a WiFi enabled phone 114, a laptop computer 116 and a desktop computer 118. In various embodiments, these mobile devices and desktop computers are able to communicate via wireless router 120 with cloud server 106 and weight management service 108.

In various embodiments, network 104 communications channels can include, but are not limited to, local area networks (LANs), wide area networks (WAN), wireless local area networks (WLAN), WiFi networks, Third Generation (3G), Fourth Generation (4G), or Fifth Generation (5G) mobile telecommunications network, or any combination of these. In other embodiments, other suitable types of networks may be used. In various embodiments, suitable communications or communications channels can include short message service (SMS) notifications, push notifications, email message communications, chat service, or any suitable web-based service. FIG. 1 also demonstrates how users are able to access their accountability circle and the dashboard and messaging features that the accountability circle provides (see also, FIG. 11).

In the illustrated embodiments, individuals can sign up for the weight management service 108 where they are asked for information such as age and height. They can enter their target weight and associated time limit as well. If a user does not enter the optional information of target weight and associated time frame to lose the weight, the weight management service will generate a target weight and the time required to reach the target weight.

The weighing device 102 is used to acquire the current and subsequent weights reading. As an individual steps on the scale 102, his/her weight is uploaded to the cloud server 106. The weight management service 108 on cloud server 106 determines whether the sub-goals for the individual are already determined. In other embodiments, two or more scales 102' may be used. In embodiments where the user has a measured weight $W_a$, that is heavier than the maximum weight that scale 102 can handle accurately, one additional scale 102' is used and the user may step on two scales, scale 102 and scale 102', and the user's current measured weight $W_a$ will be obtained by summing the weight from scale 102 with the weight from scale 102' (see also, FIGS. 7 and 13).

In the illustrated embodiments, if the individual is a new user or is beginning the weight loss process, the weight management service 108 determines the sub-goals based on the individual's requirements. If the individual has not provided a target weight, an ideal weight is estimated using an average (combination) of G. J. Hamwi Formula (1964), B. J. Devine Formula (1974), D. Robinson Formula (1983), and D. R. Miller Formula (1983).

According to the combined formula, the ideal weight in pounds for an adult is:

$$W_{men,ideal} = 113.5 + 4.5 \times (\text{height in inches} - 60)$$

$$W_{women,ideal} = 106.5 + 4.15 \times (\text{height in inches} - 60)$$

The estimated ideal weight is determined by the weight management service and shared with the individual. If the individual agrees with the suggested target weight determined by the weight management service, the weight management service uses the suggested target weight as the desired weight to be achieved for the individual. If the individual does not agree, the individual needs to provide a desired weight to the weight management service. The estimated ideal weight is designated as the Desired Weight.

Definitions $C_w$=Current Weight
$D_w$=Desired Weight
$\Delta W$=Required weight drop=$C_w - D_w$
$\tau$=Time in which $D_w$ is to be achieved
n=number of time units in progress (by default units are weeks)
r=Weight loss distribution (curve tension), this describes the distribution of weight loss from start to end. Examples shown in FIG. 8.

Figure 8:
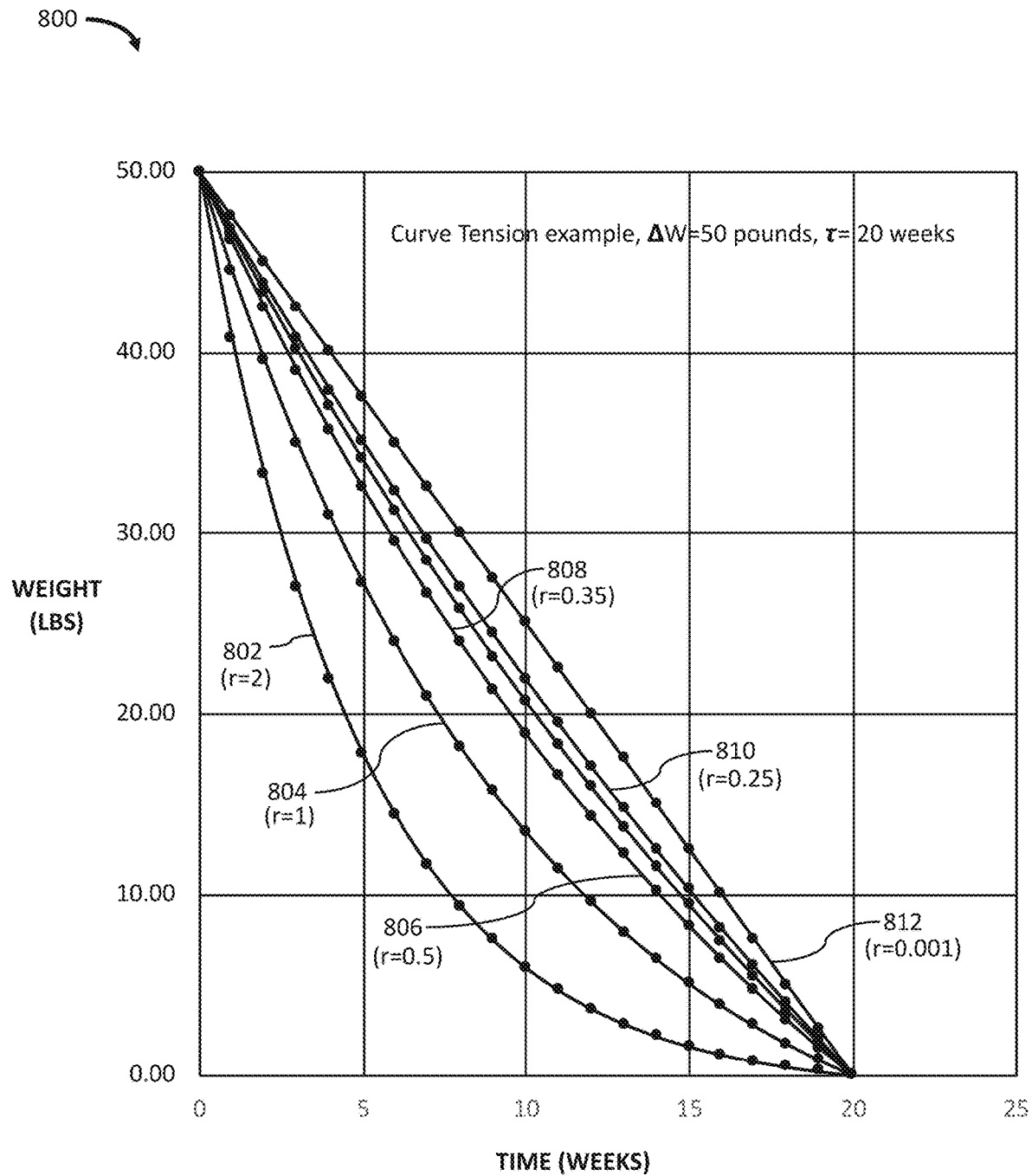
FIG. 8 illustrates embodiments of curve tension, which governs the weight loss distribution in $W\tau$ plane.

In the illustrated embodiments, curve tension is applied as described herein is used for interactive weight management by weight management service 108. FIG. 8 shows various path the individual may follow to reach the same target weight in the same time period. The behavior of distribution is dictated by r, the curve tension. FIG. 8 represents various examples for r=2.0 to r=0.001. People do not necessarily lose the same amount of weight in every time period. Generally, people lose more weight in the beginning than towards the end of a given time period during their weight loss effort. Due to a number of factors, often times, the last several pounds can be the most difficult to lose. The concept of curve tension, as described in the embodiments herein, has been found to be very meaningful and accurate in the formulation of weight loss sub-goals or for weight management in general.

In the illustrated embodiments, if the user has provided a desired weight $D_w$, and a time period $\tau$ in which $D_w$ is to be achieved, the system proceeds with the determination of the weight loss sub-goals. In the determination of the sub-goals, $\Delta W$, r, and $\tau$ are the input variables used by the weight management service. In the illustrated embodiments, the sub-goal determination formula is as follows:

Anytime weight, $W_r$, during weight loss period is modeled as $$W_r = \Delta W e^{-rn} + D_w \quad (1)$$

In the illustrated embodiments, when applying the concept of curve tension, weight loss is modeled around $e^{-x}$ due to the non-linearity of the weight loss function by an individual. The weight loss function has been found to not to be linear with time, thus a straight line or linear model will not accurately reflect the weight loss function. This is because at the beginning of the weight loss process, people or users tend to lose weight easily and quickly, and when close to a desired weight, people tend to find that the last several pounds are more difficult to lose. In the embodiments illustrated herein, the long tail of the function $e^{-x}$ is eliminated by restricting the function to operate before long tail begins.

In one exemplary embodiment, weight loss equation (2) is utilizing $e^{-2}$ functionality. The weight loss is modeled as $$W_l = \frac{\Delta W e^{-rn}}{1 - e^{-2}}$$

and transitioning the working area within $\Delta W$:

$$W_l = \frac{\Delta W e^{-rn}}{1 - e^{-2}} - \Delta W \frac{e^{-2}}{1 - e^{-2}} \quad (2)$$

In one exemplary embodiment, weight loss equation (3) is utilizing $e^{-3}$ functionality. The weight loss is modeled as $$W_l = \frac{\Delta W e^{-rn}}{1 - e^{-3}}$$

and transitioning the working area within $\Delta W$:

$$W_l = \frac{\Delta W e^{-rn}}{1 - e^{-3}} - \Delta W \frac{e^{-3}}{1 - e^{-3}} \quad (3)$$

After generalization of (2) and (3) in terms of $\tau$, the generic formula for weight loss is:

$$W_l = \frac{\Delta W}{1 - e^{-\frac{r\tau}{10}}} \left( e^{\frac{-rn}{10}} - e^{-\frac{r\tau}{10}} \right), n = \{0, 1, 2, \ldots \tau\} \text{ and } \tau, r \neq 0 \quad (4)$$

In embodiments where the user has not provided $\tau$, the time in which $D_w$ is to be achieved, $\tau$ can be determined as follows:

$$\tau = \frac{\Delta W}{1.5} \quad (5)$$

In the embodiments described herein, $\tau$ and r are dynamically adjusted and get tuned based on the user's performance in terms of meeting their weight loss sub-goals.

Sub-goals are determined using the weight drop formula as follows:

$$W_i = \frac{\Delta W}{1 - e^{-\frac{r\tau}{10}}} \left( e^{\frac{-rn}{10}} - e^{-\frac{r\tau}{10}} \right), n = \{0, 1, 2, \ldots \tau\}, W_i \text{ for } n = 0 \equiv \Delta W \quad (6)$$

In the illustrated embodiments, based on user's input, r and τ are set. In other embodiments, n is not an integer value. In some embodiments, r is automatically set to r=0.25, and r is adjusted adaptively during the weight loss effort if sub-goals are not met or if sub-goals are met well in advance. In some embodiments, if τ is not provided by the user, it is determined by equation (5).

In the illustrated embodiments, the sub-goals are set as follows:

First sub-goal $g_1$: $g_0$ to $g_1$, where $g_0 > g_1$,

Second sub-goal $g_2$: $g_1$ to $g_2$, where $g_1 > g_2$,

Last sub-goal $g_n$: $g_{n-1}$ to $g_n$, where $g_{n-1} > g_n$, where n≥2 and is any suitable number.

Figure 2:
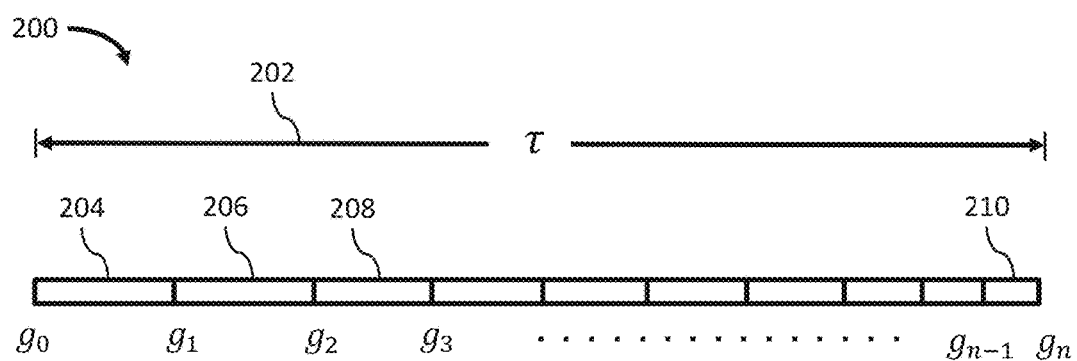
FIG. 2 depicts a pictorial view of sub-goals determination, using the formula stated in Equation (6). Input parameters are $\Delta W$, $\tau$, and r.

FIG. 2 illustrates an embodiment of sub-goal determination using equation (10) as described above. Input parameters for equation (10) are ΔW, τ, n and r. FIG. 2 illustrates a weight loss timeline in a horizontal direction at 202, where the total time between $g_0$ and $g_n$ is equal to τ as indicated, where τ is the total time in which the desired weight loss ΔW is to be achieved, and where each sub-goal weight $g_0$, $g_1$, . . . $g_n$ is determined by adding the desired weight $D_w$ to the weight calculated by equation (10). FIG. 2 also illustrates sub-goal weights, $g_0$, $g_1$, . . . $g_n$ along the horizontal timeline 202, where each successive sub-goal weight is less than a previous sub-goal weight (see also, Table 2). The sub-goal weights $g_0$, $g_1$, . . . $g_n$ represent a sub-goal weight for the end of a specific time period (e.g., 204,206, 208, 210). The sub-goal weight $g_0$ corresponds with a weight at the beginning of the first time period 204. In the illustrated embodiment, the sub-goal weight $g_0$ at the beginning of the first time period 204 corresponds with the current weight $C_w$, the sub-goal weight $g_1$ represents the sub-goal weight at the end of the first time period 204, and the sub-goal weight $g_n$ represents the sub-goal weight at end of the last time period 104. In the illustrated embodiment, the sub-goal weight at the end of the time period τ corresponds with the desired weight $D_w$. In some embodiments, a larger sub-goal is made combing two or more consecutive sub-goals. In other embodiments, the sub-goal weights $g_0$, $g_1$, . . . $g_n$ can represent a sub-goal weight for another part of a specific time period (204,206, 208, 210), such as at the beginning of the time period (204,206, 208, 210) or in the middle of the time period (204,206, 208, 210).

In the illustrated embodiment, the values of n for $g_1$, $g_2$, . . . $g_n$ correspond with the end of a time period (e.g., 204,206, 208, 210) where a user's weight is measured by weighing device 102 and compared to the assigned sub-goal weight $g_i$ for that time period. In one embodiment, if τ=20 weeks and n represents a time period in weeks, the time period 204 between $g_0$ and $g_1$ is equal to one week and the value of $g_1$ at the end of the first time week (n=1) is equal to the sub-goal weight $g_1$ at the end of the first week. In one embodiment, if τ=20 weeks and n represents a time period in weeks, the time period 206 between $g_1$ and $g_2$ is equal to one week and the value of $g_2$ at the end of the second time period 206 after two weeks have passed (n=2) is equal to the sub-goal weight $g_2$ at the end of the second week.

In the illustrated embodiment, weight loss $W_l$ is determined by using equation (6) above for $W_0$, $W_1$, . . . $W_n$ and adding the result of equation (6) to the desired weight $D_w$ as follows:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w \quad (7)$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w \quad (8)$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w = C_w \quad (9)$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w \quad (10)$$

Figure 4:
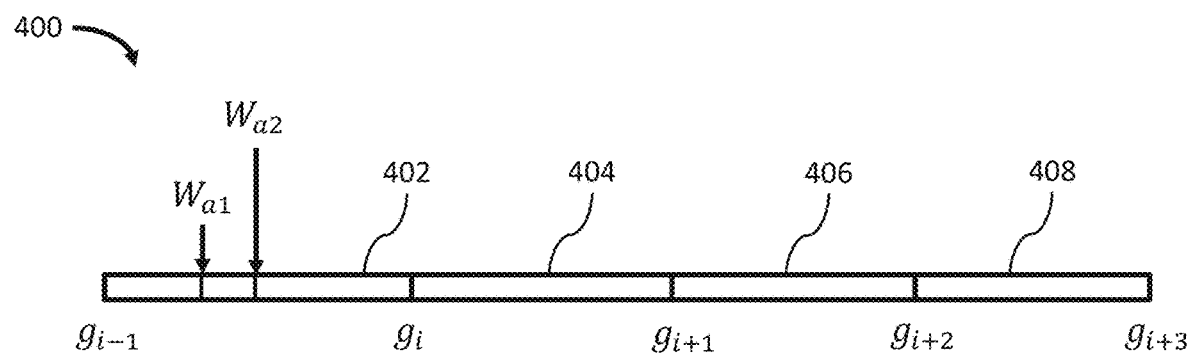
FIG. 4 demonstrates the sub-goals reassignment condition. The reassignment condition is governed by Equation (11), in which user lags behind the assigned sub-goals. After detecting this condition, the sub-goals are reassigned using updated $\Delta W$, r, and $\tau$.
Figure 5:
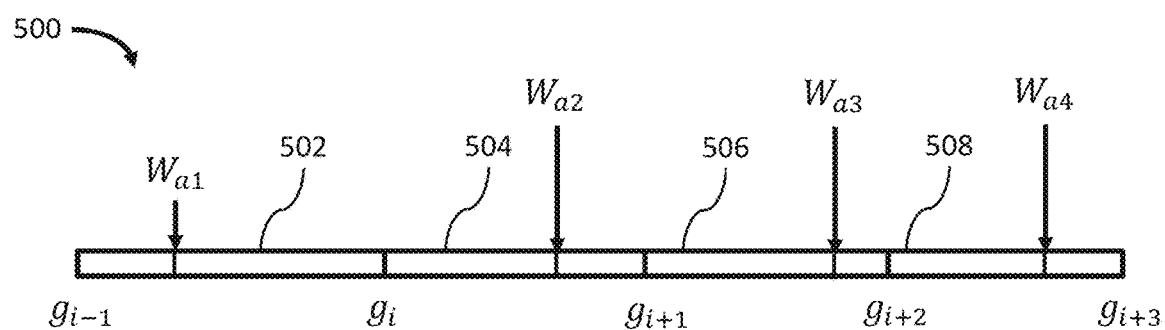
FIG. 5 shows an example in which user does not meet sub-goals several times but the user is maintaining the pace. Every time the user crosses one sub-goal. Therefore, the user does not need new sub-goals.
Figure 6:
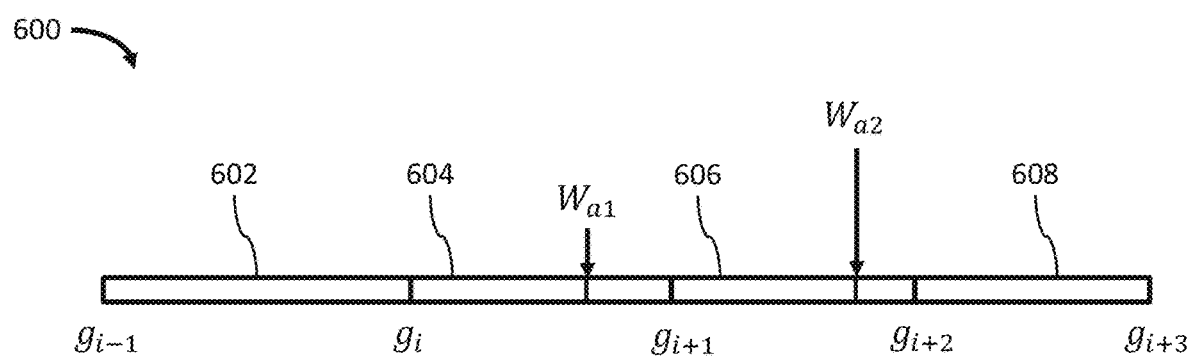
FIG. 6 demonstrates the sub-goals reassignment condition. The reassignment condition is governed by equation (12), in which user leaps ahead the assigned sub-goals, after detecting this condition the sub-goals are reassigned per equations (13) and (6).

In the illustrated embodiment, the measured weight $W_a$, of a user is determined by weighing device 102 and is illustrated in FIGS. 4-6 as $W_a$. During each time period, multiple weights may be taken within a time period and communicated to weight management service 108 via network 106. However, the last the measured weight $W_a$ within a time period (e.g., 204,206, 208, 210) that is communicated to weight management service 108 is the measured weight $W_a$ used by weight management service 108 for determination of reassignment of sub-goals $g_0$, $g_1$, . . . $g_n$. For example, for time period 204 from assigned sub-goal $g_0$ to assigned sub-goal $g_1$, the last measured weight is indicated as $W_{a1}$. In other embodiments, the measured weight $W_a$ used by weight management service 108 for determination of reassignment of sub-goals $g_0$, $g_1$, . . . $g_n$. can be the first measured weight within a time period (e.g., 204,206, 208, 210), or can be the average or median measured weight within a time period (e.g., 204,206, 208, 210).

In the illustrated embodiments, FIGS. 4, 5 and 6 illustrate placement of measured weights $W_a$, along the weight loss timeline that correspond to the value of $W_a$, relative to the value of the assigned sub-goals $g_0$, $g_1$, . . . $g_n$. For example, if measured weight $W_{a1}$ is greater than the assigned sub-goal $g_1$ for the time period 204 where n=1 (e.g., user did not meet goal weight), the measured weight $W_{a1}$ will be shown to the left of the assigned sub-goal $g_1$ as $W_{a1}$ is greater than $g_1$. In some embodiments, the placement of $W_{a1}$ corresponds to a value represented by equation (10) (see also, FIG. 3).

Figure 3:
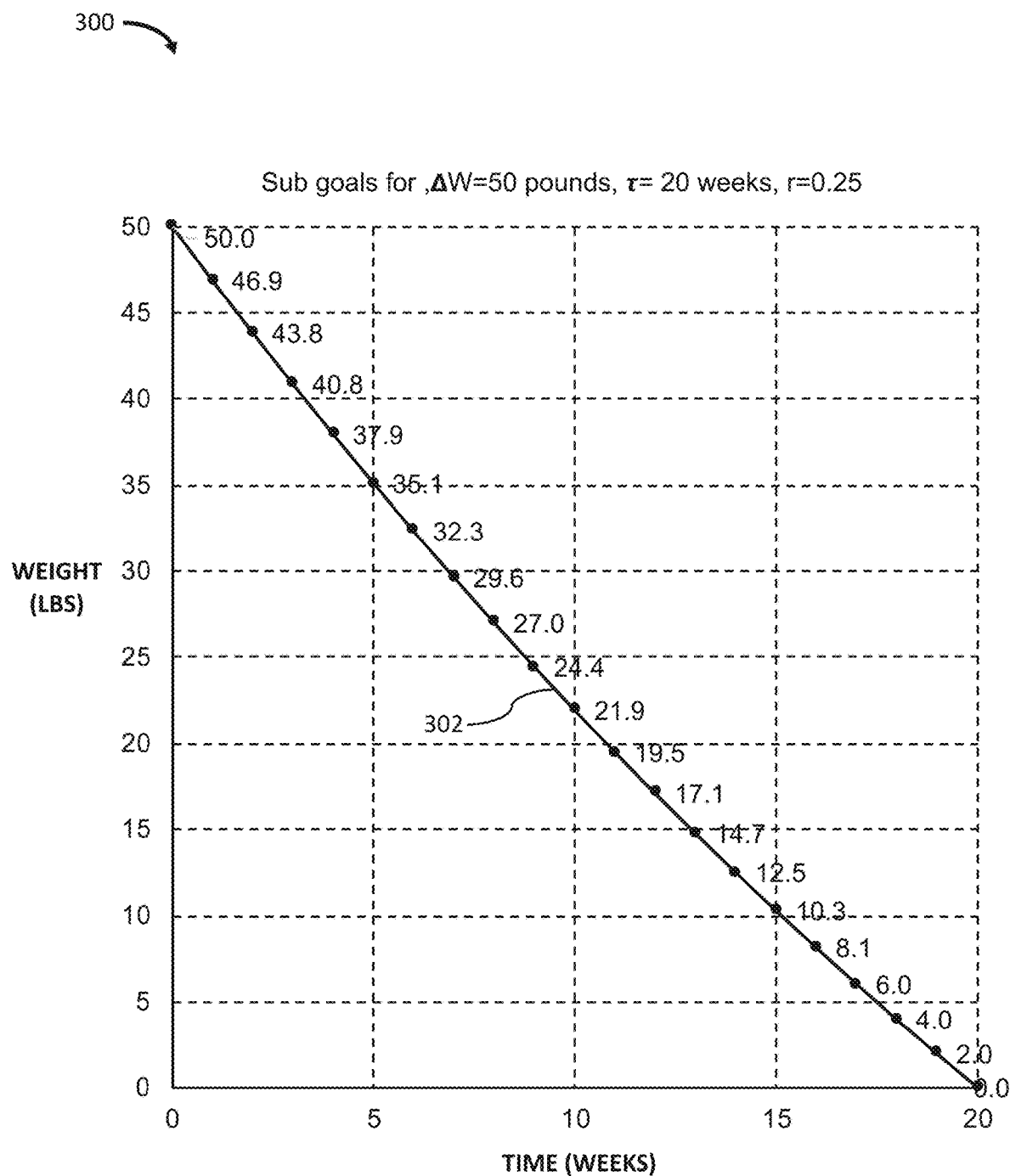
FIG. 3 shows the sub-goals in $W\tau$ plane for $\Delta W=50$ pounds, $\tau=20$ weeks, and $r=0.25$.

FIG. 3 illustrates an embodiment at 300 of sub-goals $W_0$, $W_1$, . . . $W_{20}$ generated by weight management service 108 for weight loss relative to desired weight loss ΔW is using equation (6) above in which ΔW=50 pounds, τ=20 weeks and set to r=0.25. The time, τ, is illustrated along the horizontal axis in units of weeks and weight is illustrated along the vertical axis in units of pounds.

In the illustrated embodiment, curve 302 illustrates numerical values of weight loss sub-goals $W_0$, $W_1$, . . . $W_{20}$ for which ΔW=50 pounds and illustrates an embodiment with curve tension set to r=0.25 where the weight loss for early sub-goals is greater that for trailing or later sub-goals near 20 weeks. FIG. 3 illustrates the sum of the weight loss goals for the first five weeks from week 0 to week 5 (50 pounds−35.1 pounds=14.9 pounds), is greater than the weight loss goals for the last five weeks from week 15 to week 20 (10.3 pounds−0 pounds=10.3 pounds).

In the illustrated embodiment, FIG. 3 illustrates weight loss sub-goals $W_0$, $W_1$, . . . $W_n$ to achieve the weight drop ΔW, where ΔW is equal to the current weight $C_w$ minus the desired weight $D_w$. Table 1 corresponds with FIG. 3 and illustrates an embodiment of values for $W_0, W_1, \ldots W_{20}$ for $\Delta W=50$ Lbs., r=0.25, and $\tau=20$ weeks for curve 302 as follows:

TABLE 1

| | |
|---|---|
| $W_0$ | 50.0 |
| $W_1$ | 46.8 |
| $W_2$ | 43.8 |
| $W_3$ | 40.8 |
| $W_4$ | 37.9 |
| $W_5$ | 35.1 |
| $W_6$ | 32.3 |
| $W_7$ | 29.6 |
| $W_8$ | 27.0 |
| $W_9$ | 24.4 |
| $W_{10}$ | 21.9 |
| $W_{11}$ | 19.5 |
| $W_{12}$ | 17.1 |
| $W_{13}$ | 14.7 |
| $W_{14}$ | 12.5 |
| $W_{15}$ | 10.3 |
| $W_{16}$ | 8.1 |
| $W_{17}$ | 6.0 |
| $W_{18}$ | 4.0 |
| $W_{19}$ | 2.0 |
| $W_{20}$ | 0 |

In the illustrated embodiment, FIG. 3 illustrates weight loss sub-goals weight loss sub-goals $W_0, W_1, \ldots W_n$ to achieve the weight drop $\Delta W$, where $\Delta W$ is equal to the current weight $C_w$ minus the desired weight $D_w$. The weight loss $W_l$ is set by using equation (6) above for $W_0, W_1, \ldots W_n$ as follows:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w \quad (7)$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w \quad (8)$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w = C_w \quad (9)$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w \quad (10)$$

Adding $D_w$ to $\{W_0, W_1, W_2, \ldots, W_{20}\}$ as illustrated by equations (7)-(10) yields the sub-goal weights $g_0, g_1, \ldots g_n$, shown in Table 2. Table 2 illustrates an embodiment of values for $g_0, g_1, \ldots g_{20}$, for $D_w=190$ where $\Delta W=50$ pounds, $\tau=20$ weeks, n=1 week and r=0.25 as follows

TABLE 2

| | |
|---|---|
| $g_0$ | 240 |
| $g_1$ | 236.8 |
| $g_2$ | 233.8 |
| $g_3$ | 230.8 |
| $g_4$ | 227.9 |
| $g_5$ | 225 |
| $g_6$ | 222.3 |
| $g_7$ | 219.6 |
| $g_8$ | 217 |
| $g_9$ | 214.4 |
| $g_{10}$ | 211.9 |
| $g_{11}$ | 209.4 |
| $g_{12}$ | 207.1 |
| $g_{13}$ | 204.7 |
| $g_{14}$ | 202.5 |
| $g_{15}$ | 200.3 |
| $g_{16}$ | 198.1 |
| $g_{17}$ | 196 |
| $g_{18}$ | 194 |
| $g_{19}$ | 192 |
| $g_{20}$ | 190 |

Figure 7:
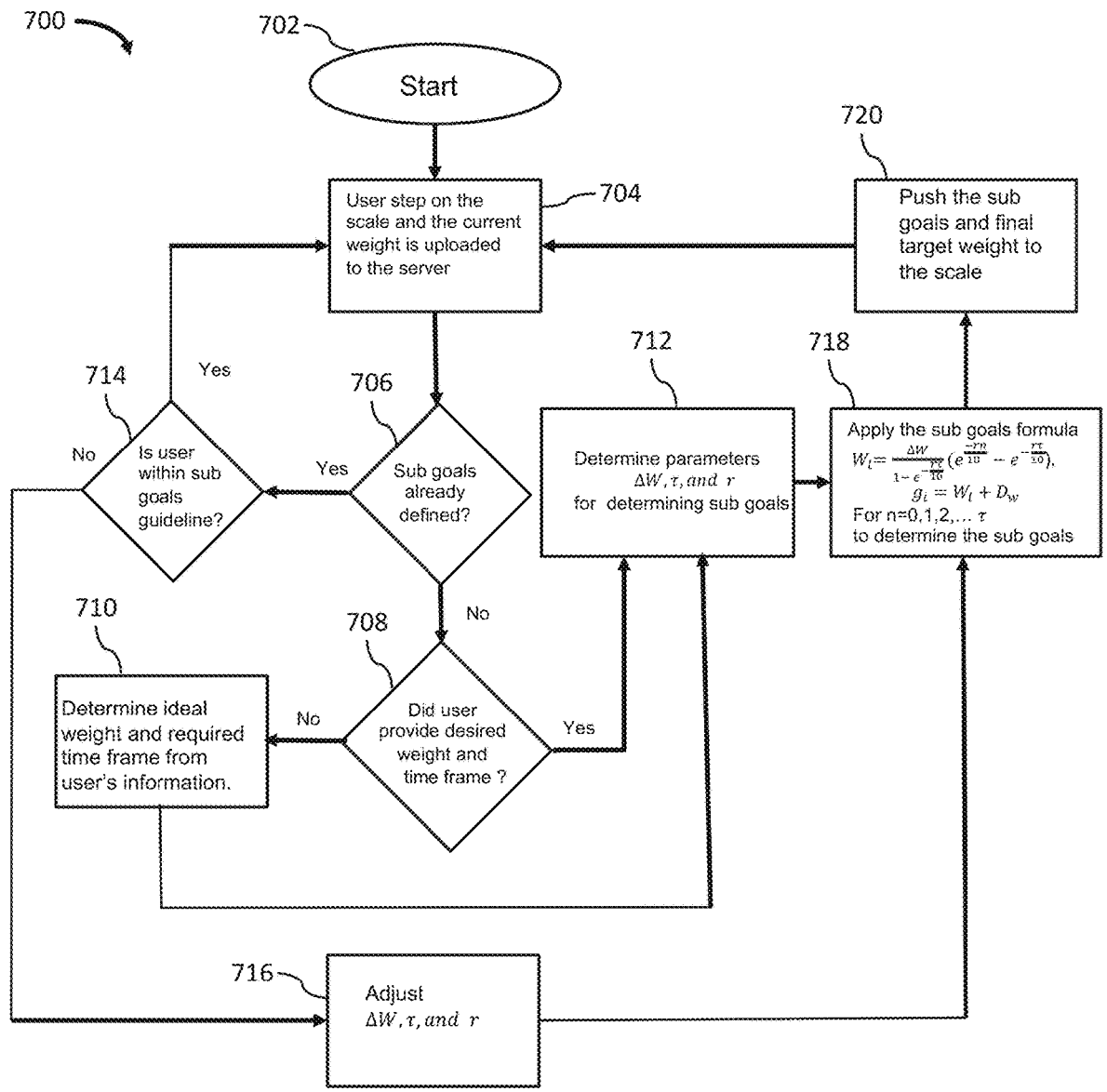
FIG. 7 depicts the flow chart of the algorithm for determining the sub-goals, detecting lagging behind or leaping ahead conditions and reassignment of the sub-goals.
Figure 13:
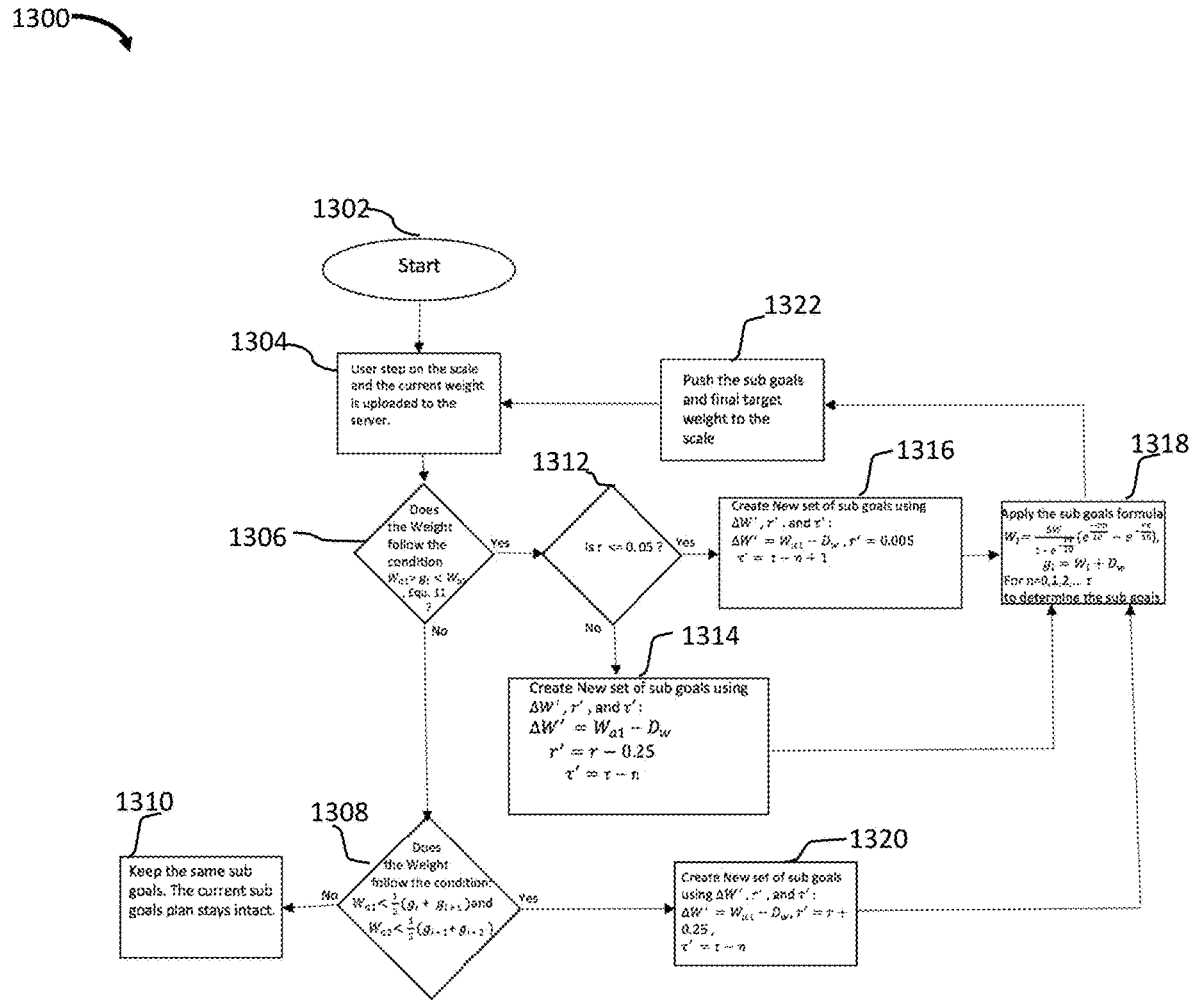
FIG. 13 shows the flow chart of an algorithm for detecting the lagging and the leaping forward conditions in achieving the sub-goals. After detecting the conditions of lagging or leaping forward, $\Delta W$, $\tau$, and r are adjusted appropriately and fed to the sub-goal generation formula.

After sub-goals are determined by weight management service 108 per equation (10), and optionally using equation (5), weight management service 108 communicates the sub-goals to weighing device 102 via network 106 where the sub-goals are stored, for periodic display, on a GUI or display on weighing device 102. In various embodiments, the sub-goals may also be communicated, via network 106, to one or more of cellular phone 110, tablet 112, WiFi enabled phone 114, laptop 116 and/or desktop computer 118, where the sub-goals are stored, for periodic display, on a GUI or display for one or more of cellular phone 110, tablet 112, WiFi enabled phone 114, laptop 116 and/or desktop computer 118. FIG. 7 and FIG. 13 illustrate further embodiments of sub-goal determinations by weight management service 108.

In the illustrated embodiment, if weight management service 108 determines a user cannot reach his/her desired weight $D_w$, via one or more measured weights $W_a$ of a user that is measured by weighing device 102 and communicated to weight management service 108 via network 106, weight management service 108 determines and assigns new sub-goal weights $g_0, g_1, \ldots g_n$ and communicates the new sub-goal weights $g_0, g_1, \ldots g_n$ to weighing device 102 via network 106 (see also FIGS. 4, 5, 6, 7 and 13). In various embodiments, the sub-goal weights $g_0, g_1, \ldots g_n$ may also be communicated, via network 106, to one or more of cellular phone 110, tablet 112, WiFi enabled phone 114, laptop 116 and/or desktop computer 118, where the sub-goals are stored, for periodic display, on a GUI or display for one or more of cellular phone 110, tablet 112, WiFi enabled phone 114, laptop 116 and/or desktop computer 118.

In the illustrated embodiments, when weight management service 108 determines new sub-goal weights $g_0, g_1, \ldots g_n$ are to be reassigned, in various embodiments, FIGS. 4, 5, 6, 7 and 13 illustrate methods and algorithms used to determine the new sub-goal weights $g_0, g_1, \ldots g_n$ that are communicated to weighing device 102 and/or one or more of cellular phone 110, tablet 112, WiFi enabled phone 114, laptop 116 and desktop computer 118 via network 106.

In two exemplary embodiments, weight management service 108 determines new sub-goal weights $g_0, g_1, \ldots g_n$ (as illustrated in FIGS. 4, 5, 6, 7 and 13) utilizing two conditions/options:

1) Keep the time to reach the ultimate goal, $\tau$, the same and change r to a lower value. This change in curve tension r will result in higher sub-goal weights $g_0, g_1, \ldots g_n$ (e.g., less weight loss between sub-goals) as determined by equation (10) with the early sub-goal weights such as $g_0, g_1$ when compared to the previous remaining sub-goal weights before reassignment of the new sub-goal weights $g_0, g_1, \ldots g_n$.

2) Update either the desired weight $D_w$, or $\tau$, the time required to achieve the weight drop $\Delta W$. Per user's choice either $\tau$ would be increased or $D_w$ would be increased to a realistic value. The condition is applied when a user is not making weight loss progress as determine by one or more of FIGS. 4, 5, 6, 7 and 13)

Various embodiments of the updates and reassignment of the sub-goal weights $g_0, g_1, \ldots g_n$ are illustrated in FIG. 13. In these embodiments, sub-goal progress is monitored and new sub-goals are assigned. During the initial setup, the desired goal and time, i.e., $D_w$ and $\tau$, would be assessed and user will be informed if $D_w$ and $\tau$ are unrealistic and will be suggested with a realistic achievable option.

FIG. 4 illustrates an embodiment at 400 of a sub-goal reassignment conditions when weight management service 108 determines new sub-goal weights $g_0, g_1, \ldots g_n$ are to be reassigned. The reassignment condition utilized by weight management service 108 is governed by equation (11) and illustrates a condition where a user's measured weights $W_{a1}$ for week i, and $W_{a2}$ for week i+1 are greater than the assigned sub-goal weight $g_i$ for two consecutive measurement periods.

In an embodiment, let $W_{a1}$ be the actual weight for the sub-goal $g_i$, and $W_{a2}$ be the actual weight for the sub-goal $g_{i+1}$. The following condition at (11) is utilized by weight management service 108 to determine if new sub-goal and reassignment weights $g_0, g_1, \ldots g_n$ are communicated to weighing device 102 and/or one or more of cellular phone 110, tablet 112, WiFi enabled phone 114, laptop 116 and desktop computer 118 via network 106:

$$W_{a1} > g_i < W_{a2} \tag{11}$$

In this embodiment, the users measured weight $W_{a2}$ was expected to be at $g_{i+1}$ but instead is greater than $g_i$ as shown in FIG. 4. This "lag" meets the reassignment condition set by equation (11), and is sufficient for weight management service 108 to determine and reassign new sub-goal weights $g_0, g_1, \ldots g_n$ and communicate the new sub-goal weights $g_0, g_1, \ldots g_n$ to weighing device 102 and/or one or more of cellular phone 110, tablet 112, WiFi enabled phone 114, laptop 116 and desktop computer 118 via network 106. Weight management service 108 determines and reassigns the new sub-goal weights $g_0, g_1, \ldots g_n$ using updated values of $\Delta W$, r, and $\tau$ as illustrated in FIG. 13.

FIG. 5 illustrates an embodiment at 500 of a sub-goal reassignment conditions when weight management service 108 determines new sub-goal weights $g_0, g_1, \ldots g_n$ are not to be assigned. In this embodiment, via measured weights $W_a$, of a user that is measured by weighing device 102 and communicated to weight management service 108 via network 106, weight management service 108 determines that a user is not meeting the assigned sub-goal weights $g_0, g_1, \ldots g_n$ but the user is also maintaining a weight loss pace as follows. In this embodiment, weight $W_{a1}$ was expected to be at $g_i$ and $W_{a2}$ was expected to be at $g_{i+1}$. Because measured weights $W_{a1}, W_{a2}, W_{a3}, W_{a4}$ are within respective time periods 502, 504, 506, 508 that correspond with sub-goal weights a $g_i, g_{i+1}, g_{i+2}, g_{i+3}$, each time the user is crossing or exceeding one of the sub-goal weights $g_0, g_1, \ldots g_n$ and is maintaining pace and sub-goals are not reassigned. In this embodiment, there are no more than one measured weights $W_{a1}, W_{a2}, W_{a3}, W_{a4}$ within a respective time periods 502, 504, 506, 508. Thus if a user misses a sub-goal weight $g_i, g_{i+1}, g_{i+2}, g_{i+3}$ for each time period (e.g., 502, 504, 506, 508), but he/she crossed or exceeded a sub-goal weight $g_i, g_{i+1}, g_{i+2}, g_{i+3}$ each time a measured weight $W_{a1}, W_{a2}, W_{a3}, W_{a4}$ was taken by weight management service 108, new sub-goals are not reassigned for the user.

FIG. 6 illustrates an embodiment at 600 of a sub-goal reassignment condition when weight management service 108 determines new sub-goal weights $g_0, g_1, \ldots g_n$ are to be assigned. In this embodiment, via measured weights $W_a$ of a user that is measured by weighing device 102 and communicated to weight management service 108 via network 106, weight management service 108 determines that a user is exceeding the assigned sub-goal weights $g_0, g_1, \ldots g_n$ for two measurement time periods 602, 604, 606, 608. The measurement time periods 602, 604, 606, 608 are shown on a horizontal axis. The reassignment condition is governed by equation (12) and illustrates a condition where a user's measured weights, $W_{a1}$ and $W_{a2}$ are less than the assigned sub-goal weight $g_i$ for two consecutive two measurement time periods 602, 604, 606, 608. In FIG. 6, measured weight $W_{a1}$ was expected to be at $g_1$ but is ahead of $g_1$ and is within time period 604, and $W_{a2}$ was expected to be at $g_{i+1}$ but is ahead of $g_{i+1}$ and is within time period 606.

The reassignment condition is determined by equation (12) and represents a situation in which user leaps ahead (e.g., loses weight more quickly) than the assigned sub-goals. After detecting this condition, the sub-goals are reassigned per equations (13) and (10).

For sub-goal $g_i$, if an individual achieves $$W_{a1} < \frac{g_i + g_{i+1}}{2} \text{ and } W_{a2} < \frac{g_{i+1} + g_{i+2}}{2} \tag{12}$$

the individual is leaping ahead and new sub-goals need to be reassigned. In this embodiment, where the user is achieving their weight loss sub-goals ahead of time, and for two consecutive measurement time periods 602, 604, 606, 608, increasing the curve tension r will result in lower sub-goal weights $g_0, g_1, \ldots g_n$ (e.g., greater weight loss) with the early sub-goal weights as compared to the previous sub-goal weights before reassignment of the new sub-goal weights $g_0, g_1, \ldots g_n$.

In this embodiment, the reassignment parameters would be:

$$\left.\begin{array}{l}\Delta W' = W_{a1} - D_w \\ r' = r + 0.25 \\ \tau' = \tau - n\end{array}\right\} \tag{13}$$

FIG. 7 depicts an embodiment at 700 for assigning sub-goal weights $g_0, g_1, \ldots g_n$. The sub-goal assignment is performed by weight management service 108 and the new sub-goal weights $g_0, g_1, \ldots g_n$ are communicated to weighing device 102 via network 104. In one embodiment, the method is executed by one or more processors located on a cloud server 106. In other embodiments, weight measurement device or scale 102 requests the cloud server 106 to send new sub-goal weights $g_0, g_1, \ldots g_n$ if new sub-goal weights $g_0, g_1, \ldots g_n$ are required for scale 102 as shown in FIG. 1 and as discussed above. The method begins at 702. At 704, a user steps on scale 102 and the user's current measured weight $W_a$, is uploaded by operation 704 to a weight management service 108 that is hosted on cloud server 106 and via a network 104.

In embodiments where the user has a measured weight $W_a$ that is heavier than the maximum weight that scale 102 can handle accurately, the user may step on two scales, scale 102 and scale 102', and the user's current measured weight $W_a$ will be obtained by summing the weight from scale 102 with the weight from scale 102'. In this embodiment, cloud server 106 and weight management service 108 is already aware via a notification from a user device as cellular phone 110, a tablet 112, a WiFi enabled phone 114, a wireless or cellular connected weighing device or scale 102, a laptop computer 116 or a desktop computer 118 that these two machines (scale 102 and scale 102') are paired. In one embodiment, the serial numbers of the two scales 102 and 102' are associated with each other. As soon as server 106 receives a measured weight $W_a$ from one of the associated scales 102, server 106 retrieves the reading of the other associated or paired scale 102'. The server 106 adds the two weights coming from scales 102 and 102' and sends back to the screens of one or both of the scales 102 and 102' the sum of the two weights which is the user's current measured weight $W_a$, and may also send other information as well.

In the illustrated embodiment, an operation 706 determines whether sub-goal weights $g_0, g_1, \ldots g_n$ have been defined for the user. Upon determining that sub-goals have not been defined, operation 708 determines whether the user has provided a desired weight $D_w$ and a time $\tau$ in which $D_w$ is to be achieved. If operation 708 determines that the user has provided a desired weight $D_w$ and a time $\tau$ in which $D_w$ is to be achieved, the operation at 712 is performed. If operation 708 determines that the user has not provided a desired weight $D_w$ and a time $\tau$ in which $D_w$ is to be achieved, operation 710 determines an ideal weight based on the equations shown in Par. [0045] and based on the user's height and current weight and the required time frame based on equation (5).

Once operation 710 determines an ideal weight and required time frame based on the user's information, the operation at 712 is performed. The operation at 712 determines the parameters $\Delta W$, $\tau$, and r for determining sub-goals per equation (10). Once the operation at 712 determines the parameters $\Delta W$, $\tau$, and r for determining sub-goals, the operation at 718 is performed.

If operation 706 determines that sub-goals have been defined for the user, the operation at 714 is performed. Operation 714 determines whether the user is within the sub-goal guidelines as determined by equations (11), (12). If operation 714 determines the user is within the sub-goal guidelines, the system waits for the next event at 704, where user's next measured weight $W_a$ is uploaded to the server 106 and weight management service 108 and discussed above. If operation 714 determines that the user is not within the sub-goal guidelines, the operation at 716 is performed. The operation 716 adjusts values of $\Delta W$, $\tau$, and r per equation (13). Once the operation at 716 has adjusted the values of $\Delta W$, $\tau$, and r, the operation at 718 is performed which is equation (10). Further details of embodiments of the update of $\Delta W$, $\tau$, and r are depicted in FIG. 13. Equation (10) is executed for n=0, 1, 2, ... $\tau$ for the condition $g_i = W_i + D_w$ as illustrated with equations (7)-(10).

Once the operation at 718 has executed the sub-goals equation (10), the operation at 720 is performed. Operation 720 pushes or sends the sub-goal weights $g_0, g_1, \ldots g_n$ and the final target weight $D_w$ to the scale 102 from cloud server 106 via network 104. Once operation 720 pushes the sub-goals and final target weight to the scale 102, the operation at 704 is performed.

FIG. 8 demonstrates an embodiment at 800 of curve tension, which governs the weight loss distribution in the $W\tau$ plane as discussed above. The higher the curve tension is (value of r), the lower the sub-goal weights $g_0, g_1, \ldots g_n$ (e.g., greater weight loss) will be for the early sub-goal weights as compared to the previous sub-goal weights before reassignment of the new sub-goal weights $g_0, g_1, \ldots g_n$. The higher the curve tension is (value of r), the more quickly weight loss is expected to be achieved for the earlier weeks and weight loss is expected to occur slowly for the trailing sub-goals.

FIG. 8 illustrates values of r=2 at 802, r=1 at 804, r=0.5 at 806, r=0.35 at 808, r=0.25 at 810 and r=0.001 at 812.

Curves 802, 804, 806, 808, 810 and 812 are determined using equation (6) above with $\Delta W$=50 Lbs. and $\tau$=20 weeks.

Figure 9:
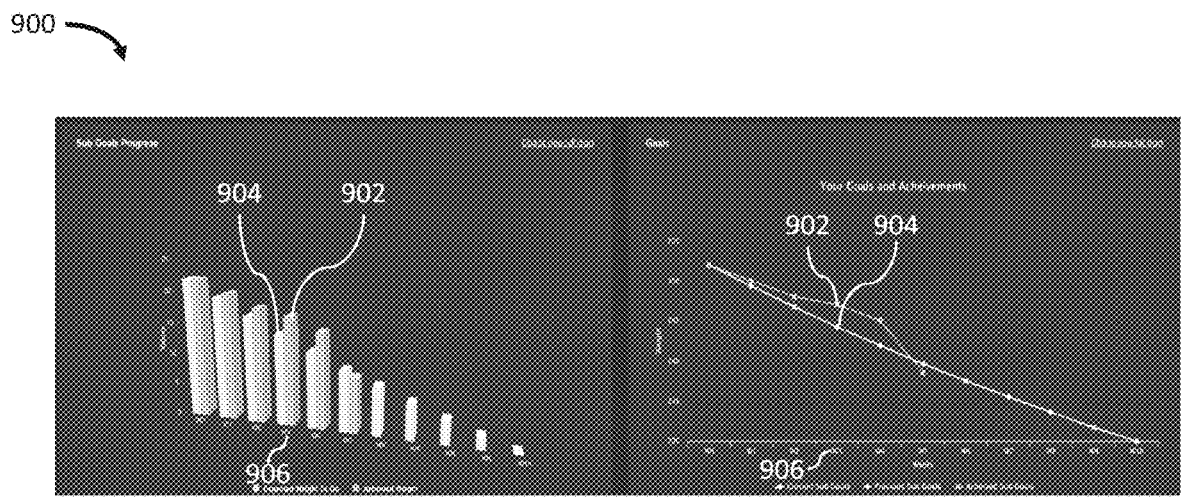
FIG. 9 depicts a portion of the user's dashboard where the system shows the target (suggested) sub-goals and how the user is achieving the sub-goals in a plot of the sub-goals and the achieved goals.

FIG. 9 illustrates an embodiment of a portion of a user dashboard at 900. User dashboard 900 illustrates assigned sub-goal weights $g_0, g_1, \ldots g_n$ and measured weights $W_a$ provided by weight management service 108 to one or more user devices such as cellular phone 110, a tablet 112, a WiFi enabled phone 114, a wireless or cellular connected weighing device or scale 102, a laptop computer 116 or a desktop computer 118, and displayed on the GUI or display of the one or more devices. In the illustrated embodiment, an exemplary measured weight $W_{a3}$ at 902 for an exemplary respective time period W3 illustrated at 906 corresponds with an exemplary sub-goal weight $g_3$ illustrated at 904 (see also, FIG. 5).

Figure 10:
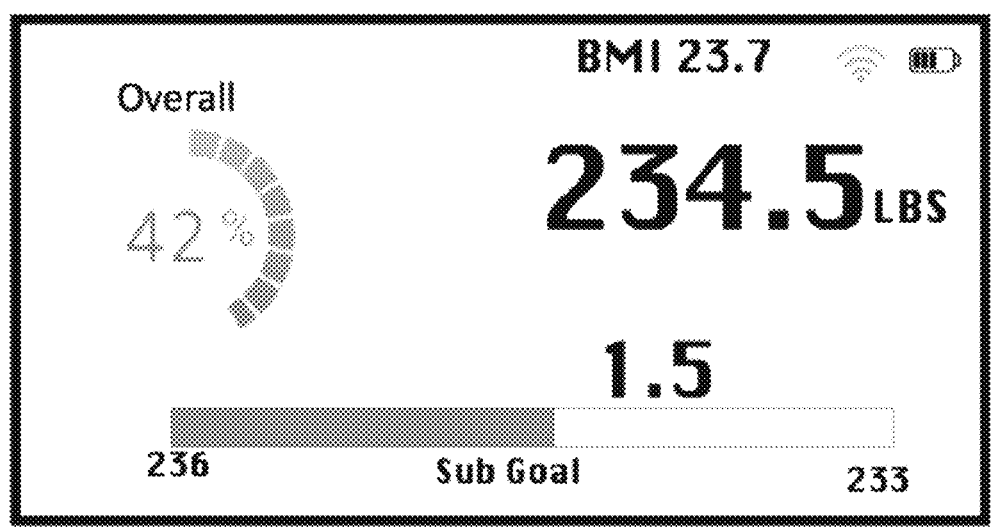
FIG. 10 shows the weighing device screen which is displayed on the dashboard as well. It shows the user's overall progress, how far the user is from the sub-goal, current BMI and current weight.

FIG. 10 illustrates an embodiment of a GUI or screen at 1000 of a weighing device 102. Information displayed on the screen 1000 may also be displayed on dashboard 900 (see also, FIG. 9). Screen 1000 illustrates the user's overall progress towards the desired weight D the status or progress of a user from meeting their sub-goal weights $g_0, g_1, \ldots g_n$, a current Body Mass Index (BMI), overall sub-goal weights $g_0, g_1, \ldots g_n$ and the user's current measured weight $W_a$. The screen 1000 or portions thereof may also be displayed on a GUI or display of one or more of cellular phone 110, tablet 112, WiFi enabled phone 114, laptop 116 and desktop computer 118.

Figure 11:
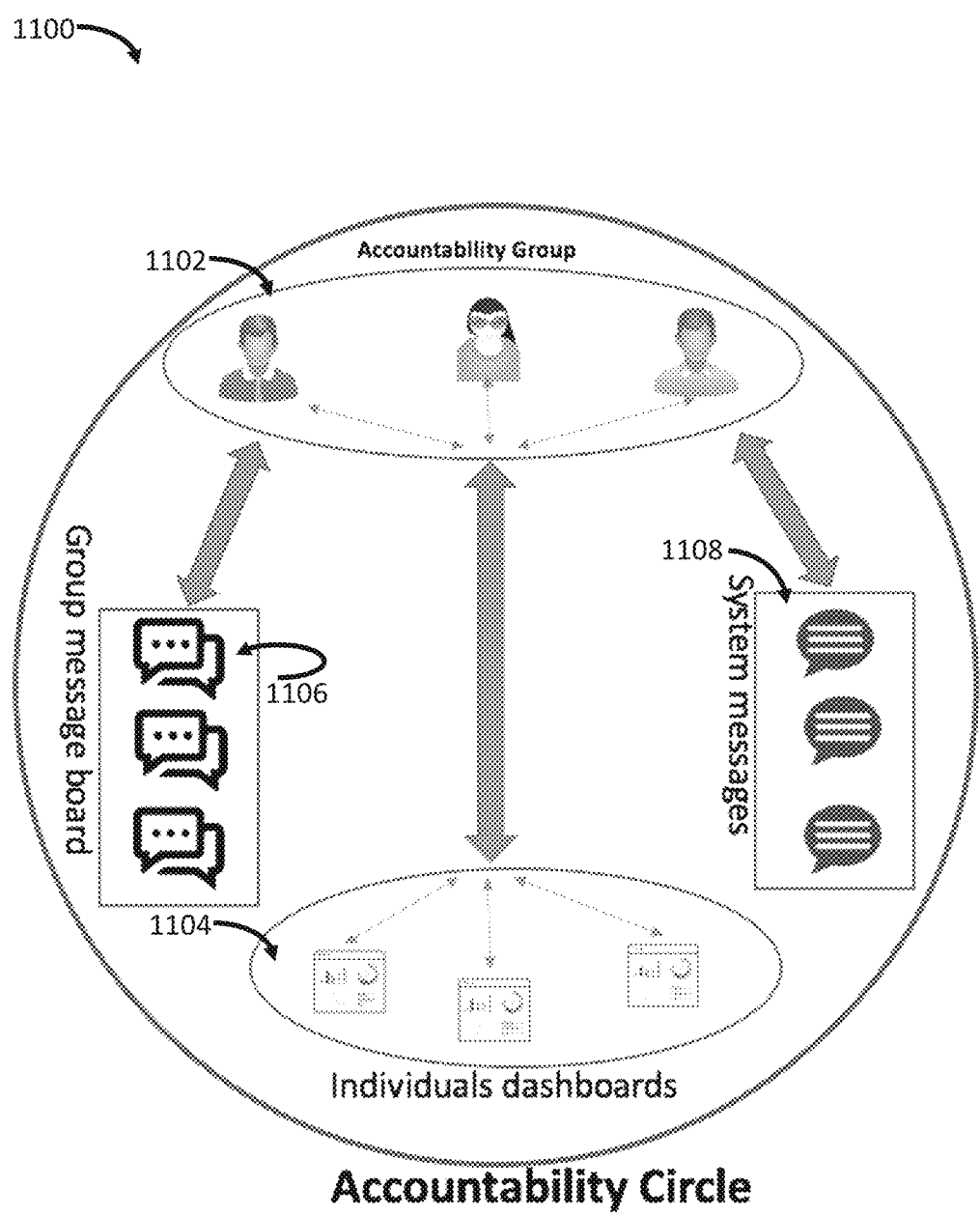
FIG. 11 depicts the concept of accountability circle, where an accountability group has access to all of its member's dashboards, access of group message board and how they can use the system messages service to communicate with one another.

FIG. 11 illustrates an embodiment of an accountability circle at 1100. With accountability circle 11, an accountability group 1102 (e.g., a number of users that have mutually agreed to be in the accountability circle) has access to all of its members dashboards illustrated at 1104 (see also, dashboard 900 in FIG. 9 and screen 1000 in FIG. 10) and access to a group message-board at 1106 and how they can communicate using system messages at 1108. In one embodiment, the level of information sharing in individual dashboards 1104 can be set by the user that initially set up the accountability circle and owns the account associated with one of the dashboards 1104.

In the illustrated embodiment, the user is encouraged to achieve weight management accountability with friend(s) or relative(s) or acquaintance(s) and setup an accountability framework, which is accountability circle 1100. The user may share his/her one of the dashboards 1104 with others with whom he/she wants to be accountable with to form an accountability group as illustrated at 1100. During the account setup via of one of cellular phone 110, tablet 112, WiFi enabled phone 114, laptop 116 and desktop computer 118 using weight management service 108 via network 104 (see also, FIG. 1). With this embodiment, users are able to setup their own permissions and the degree to which they want members with in their accountability group 1102 to view their progress and their dashboard 1104. The dashboard 1104 is accessible via a device such as cellular phone 110, tablet 112, WiFi enabled phone 114, laptop 116 via an app or https (Hyper Text Transfer Protocol Secure) that communicates with weight management service 108 running on cloud server 106. The dashboard 1104 is also accessible via desktop through World Wide Web using https via weight management service 108 running on cloud server 106 (see also, FIG. 11).

In the illustrated embodiment, the accountability group 1102 has access to a private message board 1106 where the members of accountability group 1102 can share various information or provide positive or corrective feedback to the members of the accountability group 1102. The message board 1106 is accessible via a device such as cellular phone 110, tablet 112, WiFi enabled phone 114, laptop 116 via an app or https (Hyper Text Transfer Protocol Secure) that communicates with weight management service 108 running on cloud server 106. The dashboard 1104 is also accessible via desktop through World Wide Web using https via weight management service 108 running on cloud server 106 (see also, FIG. 11).

Accountability group has access to messages 1108 where each member can chat interactively with others who are available via weight management service 108 and whom are members of the accountability group 1102. They can share their messages 1108 via weight management service 108 as they deem appropriate (see also, FIGS. 9 and 10). The messages 1108 may be sent via a device such as cellular phone 110, tablet 112, WiFi enabled phone 114, laptop 116 via an app or https (Hyper Text Transfer Protocol Secure) that communicates with weight management service 108 running on cloud server 106. The messages 1108 are also accessible via desktop through World Wide Web using https via weight management service 108 running on cloud server 106 (see also, FIG. 11).

Figure 12:
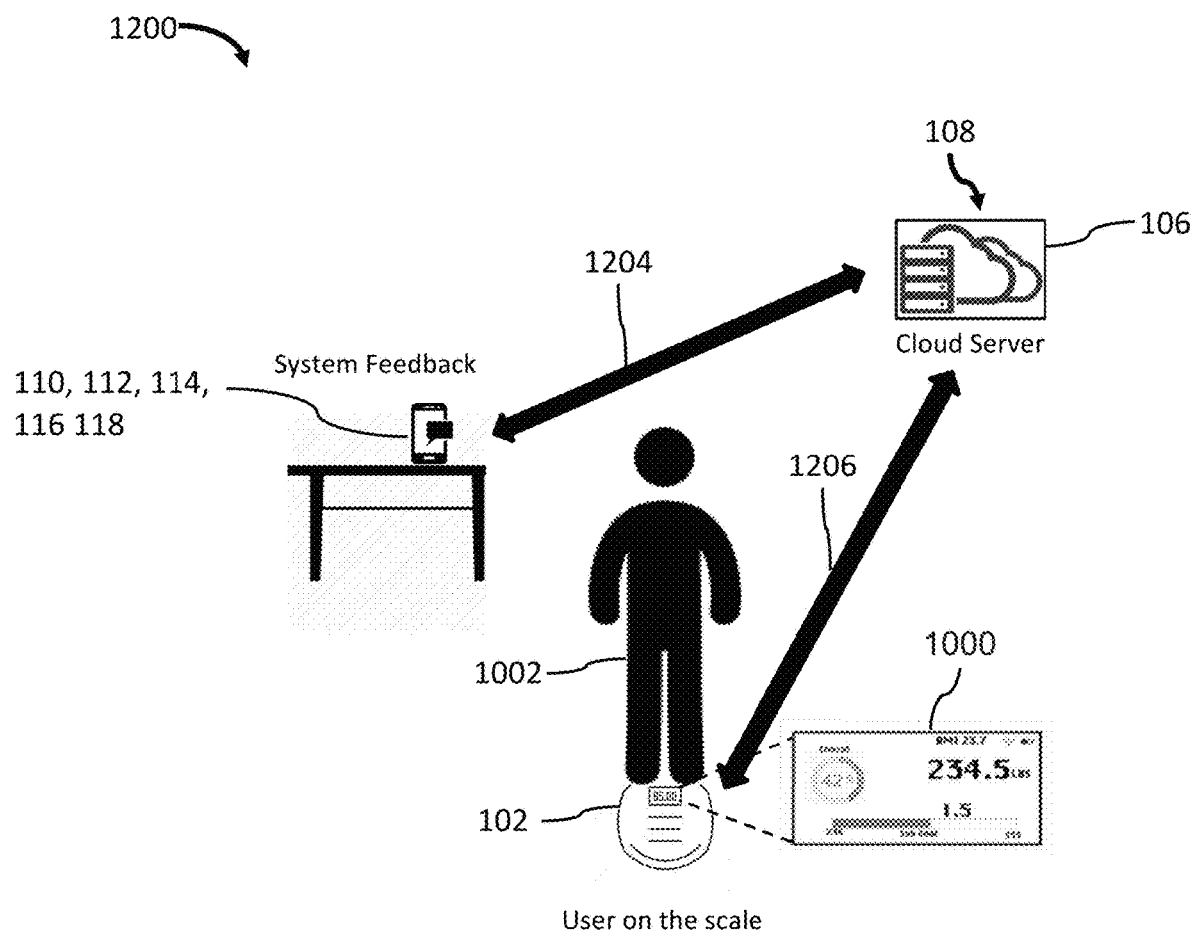
FIG. 12 shows the quick feedback mechanism. Based on the current weight cloud server sends the users a feedback on their performance and sends the weighing device new sub-goals (if needed) and overall performance.

FIG. 12 illustrates an embodiment of a quick feedback mechanism at 1200. Based on the current weight as shown on a GUI or screen 1000, the quick feedback factors can include, but are not limited to, the number of missed sub-goal weights $g_0, g_1, \ldots g_n$, the number of sub-goal weights $g_0, g_1, \ldots g_n$ that were successively achieved, BMI, height, muscle weight, fat weight, water weight and overall weight loss performance.

In the illustrated embodiment, the quick feedback information is provided through communication channel 1204 from weight management service 108, where the communication channel 1204 can include, but is not limited to, local area networks (LANs), wide area networks (WAN), wireless local area networks (WLAN), WiFi networks, Third Generation (3G), Fourth Generation (4G), or Fifth Generation (5G) mobile telecommunications network, or any combination of these (see also, FIG. 1). In the illustrated embodiment, the quick feedback information is provided to one or more of a cellular phone 110, a tablet 112, a WiFi enabled phone 114, a laptop computer 116 or a desktop computer 118 (see also, FIG. 1).

As user steps on the weighing device 102, the weight is uploaded to the cloud server 106, and weight management service 108 determines if the user 1002 is succeeding in reaching the sub-goal using equation (11) and equation (12). If user 1002 is achieving sub-goals successfully, weight management service 108 sends positive reinforcing feedback to one or more of the users 1002 devices such as cellular phone 110, tablet 112, WiFi enabled phone 114, laptop 116 and desktop computer 118. If user 1002 is lagging behind per equation (11), the weight management service 108 sends the user 1002 feedback urging the user 1002 to increase his/her physical activities and control the diet along with other tips and suggestions. Based on the number of goal misses and weight drift from the desired sub-goals, a proper message is sent. To assist the user with diet and physical activities, recipes for healthy food, selection of healthy food, running, walking, and weight training related messages are sent to the user 1002 based on user's choice in his/her profile.

FIG. 13 depicts an embodiment at 1300 for determining if a user is achieving their assigned sub-goal weights $g_0, g_1, \ldots g_n$, or lagging behind or leaping ahead of their assigned sub-goal weights $g_0, g_1, \ldots g_n$. The method is executed by one or more processor on the cloud server 106 and weight management service 108. In other embodiments, the sub-goal weights $g_0, g_1, \ldots g_n$ have already been assigned, communicated to scale 102 and displayed on a GUI or display of scale 102. The method begins at 1302. At 1304, a user steps on scale 102 and the user's current measured weight $W_a$, is uploaded by operation 1304 to weight management service 108 that is hosted on cloud server 106.

In embodiments where the user is heavier than the maximum weight that scale 102 can handle accurately, the user may step on two scales, scale 102 and scale 102', and the user's current measured weight $W_a$ is obtained by summing the weight from scale 102 with the weight from scale 102'. Cloud Server 106 already is aware through settings, registration or previous communication with scale 102 and/or scale 102' that these two machines are paired. In one embodiment, the serial numbers of the two scales are associated with each other by weight management service 108. As soon as server 106 or weight management service 108 receives a weight reading from the scale 102, server 106 or weight management service 108 retrieves the reading of the other associated or paired scale 102'. The server 106 adds the two weights coming from scales 102 and 102' and sends back to the GUI or screens of one or both of the scales 102 and 102' the sum of the two weights which is the user's current measured weight $W_a$, and may also send other information as well.

In the illustrated embodiment, an operation 1306 determines whether sub-goals are met or the user is lagging behind. This determination is achieved by the condition $W_{a1} > g_i < W_{a2}$ and as shown by equation (11). Upon determining that sub-goals and weights don't meet the lagging behind condition as shown at 1306 and equation (11), operation 1308 determines whether the user is leaping forward more quickly than the assigned sub-goal weights $g_0, g_1, \ldots g_n$ as determined by operation 1308 and/or equation (12) (see also, FIG. 7). If operation 1308 determines that the user is not leaping forward per conditions shown in 1308, new sub-goals are not required, and the previously assigned sub-goal weights $g_0, g_1, \ldots g_n$ are used. If operation 1308 determines that the user is leaping forward per conditions $W_{a1} < \frac{1}{2}(g_i + g_{i+1})$ and $W_{a2} < \frac{1}{2}(g_{i+1} + g_{i+2})$ (e.g., equation (12)), a new set of updated $\Delta W$, $\tau$, and r values are determined by operation 1320, i.e., $\Delta W' = W_{a1} - D_w$, $r' = r + 0.25$, and $\tau' = \tau - n$ which is equation (13). Operation 1318 takes these updated values $\Delta W$, $\tau$, and r and re-generates the new sub-goal weights $g_0, g_1, \ldots g_n$.

If operation 1306 determines that the user is lagging behind per the condition $W_{a1} > g_i < W_{a2}$, operation 1312 looks at the value of the curve tension r. If operation 1312 determines the value of r is ≤0.05, new set of $\Delta W$, $\tau$, and r are calculated by operation 1316. Since the user already has a lower curve tension (very close to 0), the time period in which $\Delta W$ needs to be achieved, $\tau$, is incremented by 1 and $\Delta W$ and r are updated as follows: $\Delta W' = W_{a1} - D_w$ and $r' = 0.005$. These updated parameters are fed to the operation at 1318. Once the operation 1318 has executed the sub-goals equation (10) as shown at 1318, the operation at 1322 is performed. Operation 1322 pushes or sends the new sub-goal weights $g_0, g_1, \ldots g_n$ and final target weight $D_w$ to the scale 102 from cloud server 106 and weight management service 108 via network 104. Once operation 1322 pushes the sub-goals and final target weight to the scale 102, the operation at 1304 is performed where the user steps on scale 102. If operation 1312 determines that the curve tension, r, is higher than 0.05, operation 1314 reduces the curve tension by 0.25. In other embodiments, the curve tension may be changed by 0.15 or other suitable values. Operation 1314 also updates $\Delta W$ and $\tau$ as: $\Delta W' = W_{a1} - D_w$ and $\tau' = \tau - n$. The updated parameters are fed to operation 1318 (performed by cloud server 106 and weight management service 108) which generates new sub-goal weights $g_0, g_1, \ldots g_n$ and operation 1322 pushes the updated goals and final target weight (via network 104) to the scale 102. In one embodiment, discrete values of curve tension used are 1, 0.75, 0.5, 0.25, 0.05, and 0.005. In other embodiments, other suitable values of curve tension r can be used.

Figure 14:
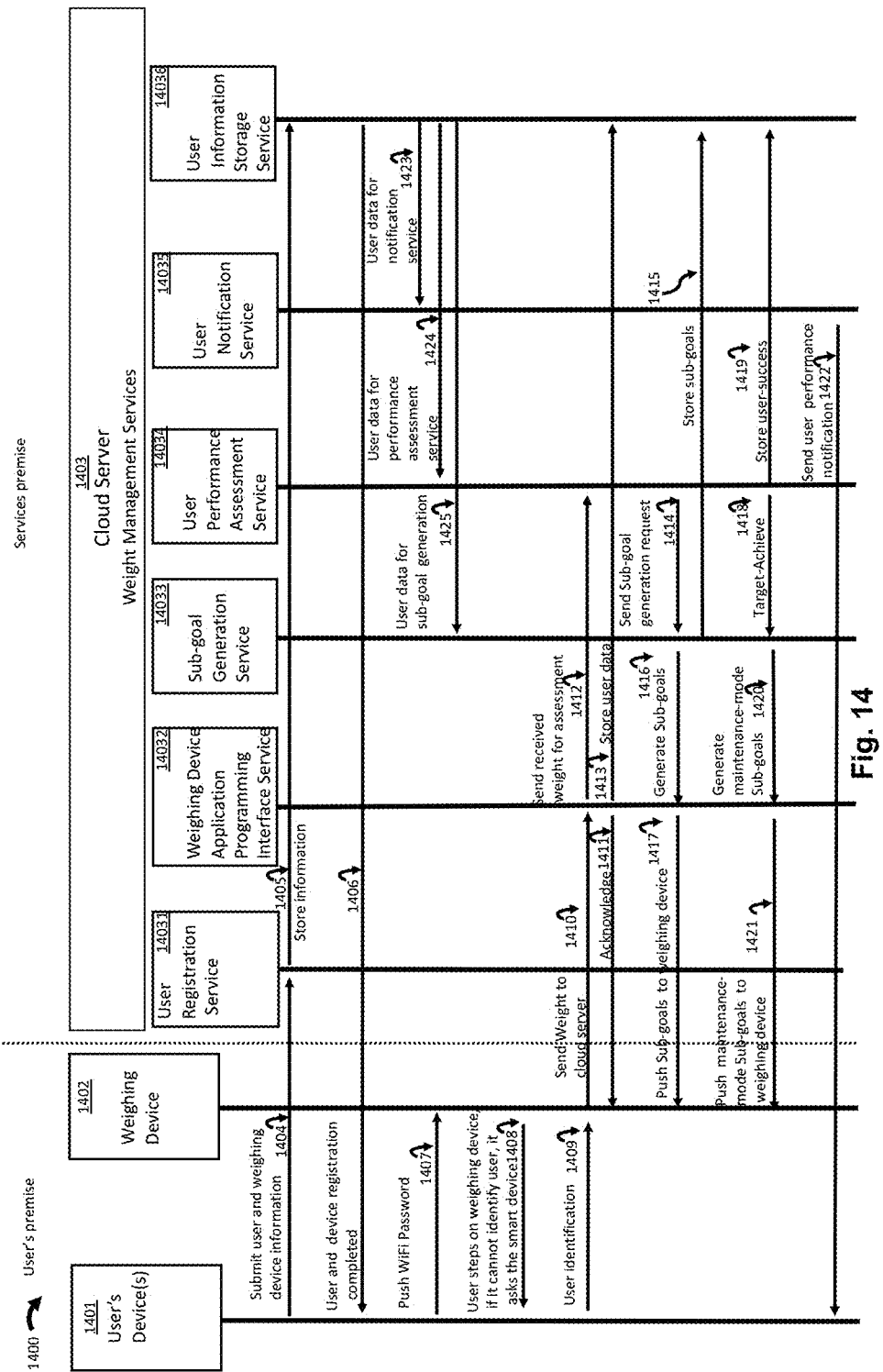
FIG. 14 shows the overall flow of the communication among the user's devices, the weighing device (scale) and the weight management services. The Weight Management Services are comprised of User Registration Service, Weight Device Application Programming Interface Service, Sub-goal Generation Service, User Performance Assessment Service, User Notification Service, and User Information Storage Service.

FIG. 14 illustrates an embodiment of an overall flow of inter-communication between a user's smart device 1401 (e.g., one or more of cellular phone 110, tablet 112, WiFi enabled phone 114, laptop 116 or desktop computer), weighing device 1402 (e.g., scale or weighing device 102), and Weight Management Services 1403 (weight management service 108 hosted on cloud server 102). In the illustrated embodiment, weight management service includes User Registration Service 14031, Weighing Device Application Programming Interface Service 14032, Sub-goal Generation Service 14033, User Performance Assessment Service 14034, User Notification Service 14035 and User Information Storage Service 14036.

In the illustrated embodiment, a user identifies user information at user device 1401 and submits the user information from user device 1401 to User Registration Service 14031. In the illustrated embodiment, content is presented at user device 1401 that allows the user to provide information that includes, but is not limited to, name, address, contact information, gender, weight management objectives, preferred units for weight and height measurement, target or desired weight ($D_w$), height, age and a weighing device serial number at 1404. The User Registration Service 14031 stores the user information and sends the user information at 1405 to User Information Storage Service 14036 for use by other services within Weight Management Service 1403. The User Information Storage Service 14036 generates an acknowledgement of the receipt of the registration at 1406 and sends the acknowledgment to the user device 1401 at 1406. In one embodiment, User device 1401 and weighing device 1402 communicate with each other using a local WiFi wireless network. In other embodiments, a cellular network may be used. In the illustrated embodiment, if the smart scale may not have a mechanism to add a WiFi SSID and password, content is presented at user device 1401 that allows a user to send the WiFi SSID and password to the weighing device 1402 at 1407. In one embodiment, the weighing device 1402 is placed in a broadcast mode that generates a broadcast channel from weighing device 1402 and the user device 1401 provides the WiFi SSID and password on the broadcast channel. Once the WiFi SSID and password are received by weighing device 1402, the broadcast channel is closed and user device 1401 and weighing device 1402 are able to communicate with each other over the WiFi network. In one embodiment, user device 1401 and weighing device 1402 can communicate over a Bluetooth network. In the illustrated embodiment, a user steps on weighing device 1402 and weighing device 1402, in response, sends the user's measured weight ($W_a$) along with the user's identification information to Weighing Device Application Programming Interface Service 14032 at 1410. If weighing device 1402 is not able to identify the user via the user's measured weight ($W_a$), weighing device 1402 communicates with user device 1401 to validate the user's identification information at 1408. User device 1401 communicates the user identification information at 1409 to weighing device 1402.

In the illustrated embodiment, Weighing Device Application Programming Interface Service 14032 sends an acknowledgement at 1411 to weighing device 1402 to confirm that the user's measured weight ($W_a$) was received by Weighing Device Application Programming Interface Service 14032. Weighing Device Application Programming Interface Service 14032 sends the user's measured weight ($W_a$) at 1412 To User Performance Assessment Service 14032. Weighing Device Application Programming Interface Service 14032 also sends the user's measured weight ($W_a$) at 1413 to User Information Storage Service 14036. In response to the user's measured weight ($W_a$) received at 1412 from Weighing Device Application Programming Interface Service 14032, the User Performance Assessment Service 14034 sends a sub-goal generation request at 1414 to sub-goal generation service 14033. The sub-goal generation request 1414 is sent, as determined by User Performance Assessment Service 14034, the first time a measured weight ($W_a$) is received at 1412, if a user is lagging behind per equation (11), or when a user is achieving sub-goals $g_0, g_1, \ldots g_n$ ahead of the assigned timeframes per equation (12).

Upon receipt of the sub-goal generation request at 1414, Sub-Goal Generation Service 14033 generates content that includes assigned sub-goals $g_0, g_1, \ldots g_n$ (see also, FIG. 9). Sub-Goal Generation Service 14033 generates the content that includes assigned sub-goals $g_0, g_1, \ldots g_n$ using equations (5), (6), (10) and (13), and as per the equations and conditions shown in FIGS. 7 and 13. The generated sub-goals $g_0, g_1, \ldots g_n$ include the timeframes between individual sub-goals $g_0, g_1, \ldots g_n$ (see also, FIGS. 2-3). In the illustrated embodiment, the sub-goals $g_0, g_1, \ldots g_n$ are generated by Sub-Goal Generation Service 14033 using equation (10). The sub-goals $g_0, g_1, \ldots g_n$ are sent at 1415 to User Information Storage Service 14036 for storage, and to Weighing Device Application Programming Interface Service 14032 at 1416. The Weighing Device Application Programming Interface Service 14032 sends the sub-goals $g_0, g_1, \ldots g_n$ at 1417 to weighing device 1402. Weighing device 1402 stores the sub-goals $g_0, g_1, \ldots g_n$ received at 1417 within a memory storage device within weighing device 1402. The weighing device 1402 displays one or more of the sub-goals $g_0, g_1, \ldots g_n$ in the associated timeframes on a GUI or display screen of the weighing device 1402.

In the illustrated embodiment, the sub-goals $g_0, g_1, \ldots g_n$ stored within weighing device 1402 are updated if the User Performance Assessment Service 14034 determines per conditions or equations (11) and (12).

Upon receipt of a user's measured weight ($W_a$) from weighing device 1402, user performance assessment service 14034 determines if the user has achieved or reached his or her desired weight ($D_w$). If the user has achieved his or her desired weight ($D_w$) as received at 1412 by User Performance Assessment Service 14034, the User Performance Assessment Service 14034 informs the sub-goal generation service 14033 at 1418 to generate maintenance mode sub-goals.

Maintenance mode sub-goals are $g_n+X$ to $g_n$, where X is small percentage of $\Delta W$. In one embodiment, X=5 pounds. In other embodiments, X can be any suitable number.

In the illustrated embodiment, the maintenance mode sub-goals are sent from the sub-goal generation service 14033 at 1420 to the Weighing Device Application Programming Interface Service 14032. The Weighing Device Application Programming Interface Service 14032 sends the maintenance mode sub-goals at 1421 to weighing device 1402.

The User Performance Assessment Service 14034 assesses the measured weight ($W_a$) received at 1412. If the measured weight ($W_a$) is greater than $g_n+X$, the user is taken out of maintenance mode and put into the normal weight loss mode and new sub-goals $g_0, g_1, \ldots g_n$ are generated by Sub-Goal Generation Service 14034 based on measured weight ($W_a$) and equations (5), (6), (10) and (13). The new sub-goals $g_0, g_1, \ldots g_n$ are sent at 1415 to User Information Storage Service 14036 for storage, and to Weighing Device Application Programming Interface Service 14032 at 1416. The Weighing Device Application Programming Interface Service 14032 sends the sub-goals $g_0, g_1, \ldots g_n$ at 1417 to weighing device 1402.

Once the user has achieved his or her desired weight ($D_w$), and in response to the user's measured weight ($W_a$) being received at 1410 from weighing device 1402 by Weighing Device Application Programming Interface Service (or simply Application Programming Interface Service) 14032, Application Programming Interface Service 14032 sends the received measured weight ($W_a$) at 1412 to User Performance Assessment Service 14034 and the User Performance Assessment Service 14034 informs the Sub-Goal Generation Service 14033 at 1416 to generate new maintenance mode sub-goals $g_n+X$, $g_n$, for the user. This process continues when weighing device 1402 sends the user's measured weight ($W_a$) at 1410 to Weighing Device Application Programming Interface Service 14032 and User Performance Assessment Service 14034 continues to assess the measured weight ($W_a$).

In the illustrated embodiment, each time a user steps on weighing device 1402, User Notification Service 14035 generates quick feedback content that is based on the number of missed sub-goal weights $g_0, g_1, \ldots g_n$, the number of sub-goal weights $g_0, g_1, \ldots g_n$ that were successively achieved, BMI, height, muscle weight, fat weight, water weight and overall weight loss performance. User Notification Service 14035 sends a notification at 1422 that is based, at least in part, on the quick feedback content. The notification sent at 1422 can include, but is not limited to, text, pictures or images, charts, URL's, and videos.

In the illustrated embodiment, User Information Storage Service 14036 provides user information or user data to the User Notification Service 14035 at 1423, the User Performance Assessment Service 14034 at 1424, and the Sub-Goal Generation Service 14033 at 1425.

The detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIGS. 1 through 13. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With the above range of variations and applications in mind, it should be understood that the present invention is not limited by the foregoing description, nor is it limited by the accompanying drawings. Instead, the present invention is limited only by the following claims and their legal equivalents.

What is claimed is:

1. A method, comprising:

submitting, over a network, from a user device that is associated with a user to a cloud server that includes one or more processors, a desired weight $D_w$ for the user and a timeframe ($\tau$) in which the a desired weight $D_w$ is to be achieved, wherein the desired weight $D_w$ and the timeframe ($\tau$) are identified or entered by the user via a Graphical User Interface (GUI) on the user device;

generating, by one or more processors, a number of sub-goal weights $g_0, g_1, \ldots g_n$ based on a current weight $C_w$, a desired weight loss amount ($\Delta W$), the desired weight $D_w$, a curve tension r which is set to an initial value that is greater than zero, and the timeframe ($\tau$) in which the weight loss amount ($\Delta W$) is to be achieved, wherein the timeframe ($\tau$) includes a number (n) of time periods that each correspond with a pair of successive ones of the sub-goal weights $g_0, g_1, \ldots g_n$ such that sub-goal weight $g_0$ corresponds with a beginning of the first one of the number (n) of time periods and sub-goal weight $g_n$ corresponds with an end of the last one of the number (n) of time periods, and wherein the sub-goal weights $g_0, g_1, \ldots g_n$ are generated by the one or more processors using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w;$$

sending, by the one or more processors, the sub-goal weights $g_0, g_1, \ldots g_n$ and the number of time periods that each correspond with the pair of successive ones of the sub-goal weights $g_0, g_1, \ldots g_n$ to a weight measuring device that is associated with the user;

receiving, by the one or more processors, one of a number of measured weights $W_0, W_1, \ldots W_n$ from the weight measuring device that is associated with the user, wherein the one of the number of measured weights $W_0, W_1, \ldots W_n$ is measured by the weight measuring device that is associated with the user, wherein each one of the number of measured weights $W_0, W_1, \ldots W_n$ is associated with a corresponding one of the number of sub-goal weights $g_0, g_1, \ldots g_n$ for a same one of the number (n) of time periods, and wherein each one of the sub-goal weights $g_0, g_1, \ldots g_n$ represents a short term desired weight for an associated one of the number of measured weights $W_0, W_1, \ldots W_n$; and displaying, on a screen of the weight measuring device, the one of the number of measured weights $W_0, W_1, \ldots W_n$ n and the corresponding one of the number of sub-goal weights $g_0, g_1, \ldots g_n$ that represents the short term desired weight for the associated one of the number of measured weights $W_0, W_1, \ldots W_n$ to indicate a progress of the user towards achieving the short term desired weight.

2. The method of claim 1, further comprising determining, by the one or more processors, if at least two of the consecutive ones of the number of measured weights $W_0, W_1, \ldots W_n$ have been received from the weight measuring device that is associated with the user, and if the condition $W_{a1} > g_i < W_{a2}$ is true, wherein $W_{a1}$ and $W_{a2}$ are the at least two of the consecutive ones of the number of measured weights $W_0, W_1, \ldots W_n$ and $g_i$ is the one of the number of sub-goal weights $g_0, g_1, \ldots g_n$ which corresponds to $W_{a1}$.

3. The method of claim 2, further comprising, if the one or more processors determines that the condition $W_{a1} > g_i < W_{a2}$ is true, generating, by the one or more processors, the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

4. The method of claim 2, wherein if the one or more processors determine that the value of r is ≤0.05, then the one or more processors increments the timeframe ($\tau$) by 1, $\Delta W$ is set to $W_{a1} D_w$ and the curve tension r is reduced to a value that is between the initial value and zero; and generating, by the one or more processors, the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

5. The method of claim 2, wherein if the one or more processors determine that the value of r is >0.05, then the one or more processors decreases the curve tension r by 0.15, $\Delta W$ is set to $W_{a1} - D_w$, and the new timeframe ($\tau$) is set to the previous timeframe ($\tau$)-n; and generating, by the one or more processors, the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

6. The method of claim 1, further comprising determining, by the one or more processors, if at least two of the consecutive ones of the number of measured weights $W_0, W_1, \ldots W_n$ have been received from the weight measuring device that is associated with the user, and if the condition $W_{a1} < g_i + g_{i+1}/2$ and $W_{a2} < g_{i+1} + g_{i+2}/2$ is true, wherein $W_{a1}$ and $W_{a2}$ are the at least two of the consecutive ones of the number of measured weights $W_0, W_1, \ldots W_n$ that correspond with $g_i$, $g_{i+1}$ and $g_{i+2}$ which are the short term desired weights for the consecutive ones of the associated measured weights $W_0, W_1, \ldots W_n$.

7. The method of claim 6, further comprising, if the one or more processors determines that the condition $$W_{a1} < \frac{g_i + g_{i+1}}{2} \text{ and } W_{a2} < \frac{g_{i+1} + g_{i+2}}{2}$$

is true, generating, by the one or more processors, the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w,$$

and wherein $\Delta W = W_{a1} - D_w$, $r = r + 0.25$ and $\tau = \tau - n$.

8. A computer program product embodied in a computer readable storage device and comprising instructions that when executed by a processor, cause the processor to:

submit, over a network, from a user device that is associated with a user to a cloud server that includes one or more processors, a desired weight $D_w$ for the user and a timeframe ($\tau$) in which the a desired weight $D_w$ is to be achieved, wherein the desired weight $D_w$ and the timeframe ($\tau$) are identified or entered by the user via a Graphical User Interface (GUI) on the user device;

generate, by one or more processors, a number of sub-goal weights $g_0, g_1, \ldots g_n$ based on a current weight $C_w$, a desired weight loss amount ($\Delta W$), the desired weight $D_w$, a curve tension r which is set to an initial value that is greater than zero, and the timeframe ($\tau$) in which the weight loss amount (ΔW) is to be achieved, wherein the timeframe (τ) includes a number (n) of time periods that each correspond with a pair of successive ones of the sub-goal weights $g_0, g_1, \ldots g_n$ such that sub-goal weight $g_0$ corresponds with a beginning of the first one of the number (n) of time periods and sub-goal weight $g_n$ corresponds with an end of the last one of the number (n) of time periods, and wherein the sub-goal weights $g_0, g_1, \ldots g_n$ are generated by the one or more processors using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w;$$

send the sub-goal weights $g_0, g_1, \ldots g_n$ and the number of time periods that each correspond with the pair of successive ones of the sub-goal weights $g_0, g_1, \ldots g_n$ to a weight measuring device that is associated with the user;

receive one of a number of measured weights $W_0, W_1, \ldots W_n$ from the weight measuring device that is associated with the user, wherein the one of the number of measured weights $W_0, W_1, \ldots W_n$ is measured by the weight measuring device that is associated with the user, wherein each one of the number of measured weights $W_0, W_1, \ldots W_n$ is associated with a corresponding one of the number of sub-goal weights $g_0, g_1, \ldots g_n$ for a same one of the number (n) of time periods, and wherein each one of the sub-goal weights $g_0, g_1, \ldots g_n$ represents a short term desired weight for an associated one of the number of measured weights $W_0, W_1, \ldots W_n$; and display, on a screen of the weight measuring device, the one of the number of measured weights $W_0, W_1, \ldots W_n$ and the corresponding one of the number of sub-goal weights $g_0, g_1, \ldots g_n$ that represents the short term desired weight for the associated one of the number of measured weights $W_0, W_1, \ldots W_n$ to indicate a progress of the user towards achieving the short term desired weight.

9. The computer program product of claim 8, further comprising determining if at least two of the consecutive ones of the number of measured weights $W_0, W_1, \ldots W_n$ have been received from the weight measuring device that is associated with the user, and if the condition $W_{a1} > g_i < W_{a2}$ is true, wherein $W_{a1}$ and $W_{a2}$ are the at least two of the consecutive ones of the number of measured weights $W_0, W_1, \ldots W_n$, and $g_i$ is the one of the number of sub-goal weights $g_0, g_1, \ldots g_n$ which corresponds to $W_{a1}$.

10. The computer program product of claim 9, further comprising, if the condition $W_{a1} > g_i < W_{a2}$ is true, generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

-continued $$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

11. The computer program product of claim 9, wherein if the value of r is ≤0.05, the timeframe (τ) is incremented by 1, ΔW is set to $W_{a1} - D_w$ and the curve tension r is reduced to a value that is between the initial value and zero; and generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

12. The computer program product of claim 9, wherein if the value of r is >0.05, then the curve tension r is decreased by 0.15, ΔW is set to $W_{a1} - D_w$, and the new timeframe (τ) is set to the previous timeframe (τ)-n; and generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

13. The computer program product of claim 8, further comprising determining if at least two of the consecutive ones of the number of measured weights $W_0, W_1, \ldots W_n$ have been received from the weight measuring device that is associated with the user, and if the condition $$W_{a1} < \frac{g_i + g_{i+1}}{2} \text{ and } W_{a2} < \frac{g_{i+1} + g_{i+2}}{2}$$

is true, wherein $W_{a1}$ and $W_{a2}$ are the at least two of the consecutive ones of the number of measured weights $W_0, W_1, \ldots W_n$ that correspond with $g_i, g_{i+1}$ and $g_{i+2}$ which are the short term desired weights for the consecutive ones of the associated measured weights $W_0, W_1, \ldots W_n$.

14. The computer program product of claim 13, further comprising, if the condition $$W_{a1} < \frac{g_i + g_{i+1}}{2} \text{ and } W_{a2} < \frac{g_{i+1} + g_{i+2}}{2}$$

is true, generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w,$$

and wherein $\Delta W = W_{a1} - D_w$, $r = r + 0.25$ and $\tau = \tau - n$.

15. A system, comprising:
one or more processors: and
one or more memory elements including instructions that when executed cause the one or more processors to:
submit, over a network, from a user device that is associated with a user to a cloud server that includes one or more processors, a desired weight $D_w$ for the user and a timeframe ($\tau$) in which the a desired weight $D_w$ is to be achieved, wherein the desired weight $D_w$ and the timeframe ($\tau$) are identified or entered by the user via a Graphical User Interface (GUI) on the user device;
generate a number of sub-goal weights $g_0, g_1, \ldots g_n$ based on a current weight $C_w$, a desired weight loss amount ($\Delta W$), the desired weight $D_w$, a curve tension r which is set to an initial value that is greater than zero, and the timeframe ($\tau$) in which the weight loss amount ($\Delta W$) is to be achieved, wherein the timeframe ($\tau$) includes a number (n) of time periods that each correspond with a pair of successive ones of the sub-goal weights $g_0, g_1, \ldots g_n$ such that sub-goal weight $g_0$ corresponds with a beginning of the first one of the number (n) of time periods and sub-goal weight $g_n$ corresponds with an end of the last one of the number (n) of time periods, and wherein the sub-goal weights $g_0, g_1, \ldots g_n$ are generated by the one or more processors using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w;$$

send the sub-goal weights $g_0, g_1, \ldots g_n$ and the number of time periods that each correspond with the pair of successive ones of the sub-goal weights $g_0, g_1, \ldots g_n$ to a weight measuring device that is associated with the user;

receive one of a number of measured weights $W_0, W_1, \ldots W_n$ from the weight measuring device that is associated with the user, wherein the one of the number of measured weights $W_0, W_1, \ldots W_n$ is measured by the weight measuring device that is associated with the user, wherein each one of the number of measured weights $W_0, W_1, \ldots W_n$ is associated with a corresponding one of the number of sub-goal weights $g_0, g_1, \ldots g_n$ for a same one of the number (n) of time periods, and wherein each one of the sub-goal weights $g_0, g_1, \ldots g_n$ represents a short term desired weight for an associated one of the number of measured weights $W_0, W_1, \ldots W_n$ and displaying, on a screen of the weight measuring device, the one of the number of measured weights $W_0, W_1, \ldots W_n$ and the corresponding one of the number of sub-goal weights $g_0, g_1, \ldots g_n$ that represents the short term desired weight for the associated one of the number of measured weights $W_0, W_1, \ldots W_n$ indicate a progress of the user towards achieving the short term desired weight.

16. The system of claim 15, further comprising determining if at least two of the consecutive ones of the number of measured weights $W_0, W_1, \ldots W_n$ have been received from the weight measuring device that is associated with the user, and if the condition $W_{a1} > g_i < W_{a2}$ is true, wherein $W_{a1}$ and $W_{a2}$ are the at least two of the consecutive ones of the number of measured weights $W_0, W_1, \ldots W_n$, and $g_i$ is the one of the number of sub-goal weights $g_0, g_1, \ldots g_n$ which corresponds to $W_{a1}$.

17. The system of claim 16, further comprising, if the condition $W_{a1} > g_i < W_{a2}$ is true, generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

18. The system of claim 16, wherein
if the value of r is ≤0.05, then the timeframe ($\tau$) is incremented by 1,
$\Delta W$ is set to $W_{a1} - D_w$ and the curve tension r is reduced to a value that is between the initial value and zero; and
generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

19. The system of claim 16, wherein
if the value of r is >0.05, then the curve tension r is decreased by 0.15,
ΔW is set to $W_{a1}-D_w$, and the new timeframe (τ) is set to the previous timeframe (τ)-n; and
generating, by the one or more processors, the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w.$$

20. The system of claim 15, further comprising if at least two of the consecutive ones of the number of measured weights $W_0, W_1, \ldots W_n$ have been received from the weight measuring device that is associated with the user, and if the condition $$W_{a1} < \frac{g_i + g_{i+1}}{2} \text{ and } W_{a2} < \frac{g_{i+1} + g_{i+2}}{2}$$

is true, wherein $W_{a1}$ and $W_{a2}$ are the at least two of the consecutive ones of the number of measured weights $W_0, W_1, \ldots W_n$ that correspond with $g_i, g_{i+1}$ and $g_{i+2}$ which are the short term desired weights for the consecutive ones of the associated measured weights $W_0, W_1, \ldots W_n$, then generating the sub-goal weights $g_0, g_1, \ldots g_n$ using the sub-goal generation formulas:

$$g_0 = W_0 + D_w = \frac{\Delta W}{1 - e^{-\frac{r\tau}{10}}}\left(e^{\frac{0}{10}} - e^{-\frac{r\tau}{10}}\right) + D_w = C_w,$$

$$g_1 = W_1 + D_w = \frac{\Delta W}{1 - e^{-\frac{r\tau}{10}}}\left(e^{\frac{-r}{10}} - e^{-\frac{r\tau}{10}}\right) + D_w,$$

$$g_2 = W_2 + D_w = \frac{\Delta W}{1 - e^{-\frac{r\tau}{10}}}\left(e^{\frac{-2r}{10}} - e^{-\frac{r\tau}{10}}\right) + D_w, \text{ and}$$

$$g_n = W_n + D_w = \frac{\Delta W}{1 - e^{-\frac{r\tau}{10}}}\left(e^{\frac{-nr}{10}} - e^{-\frac{r\tau}{10}}\right) + D_w = D_w,$$

and wherein $\Delta W = W_{a1} - D_w$, r=r+0.25 and τ=τ-n.

\* \* \* \* \*